United States Patent
Crawford et al.

(10) Patent No.: US 12,188,926 B2
(45) Date of Patent: Jan. 7, 2025

(54) STIMULI RESPONSIVE MICROSPHERE COMPOSITES

(71) Applicant: South Dakota Board of Regents, Pierre, SD (US)

(72) Inventors: Grant A Crawford, Rapid City, SD (US); George G. Wicks, Aiken, SC (US); Forest Thompson, Rapid City, SD (US)

(73) Assignees: SOUTH DAKOTA BOARD OF REGENTS, Pierre, SD (US); APPLIED RESEARCH CENTER, Aiken, SC (US)

( * ) Notice: Subject to any disclaimer, the term of this patent is extended or adjusted under 35 U.S.C. 154(b) by 472 days.

(21) Appl. No.: 16/518,489

(22) Filed: Jul. 22, 2019

(65) Prior Publication Data
US 2020/0025747 A1    Jan. 23, 2020

Related U.S. Application Data

(60) Provisional application No. 62/702,138, filed on Jul. 23, 2018.

(51) Int. Cl.
| | | |
|---|---|---|
| *G01N 33/52* | (2006.01) | |
| *A61K 9/00* | (2006.01) | |
| *A61K 9/50* | (2006.01) | |

(52) U.S. Cl.
CPC .......... *G01N 33/52* (2013.01); *A61K 9/0009* (2013.01); *A61K 9/5084* (2013.01)

(58) Field of Classification Search
CPC ..... A61K 9/0009; A61K 9/5084; B41M 3/14; B42D 25/369; B42D 25/373; B42D 25/387; C09D 11/037; C09D 11/322
See application file for complete search history.

(56) References Cited

U.S. PATENT DOCUMENTS

| | | | | |
|---|---|---|---|---|
| 7,666,807 B2 * | 2/2010 | Heung | ............... | B01D 67/0058 502/262 |
| 2005/0019556 A1 * | 1/2005 | Freeman | .......... | G06K 19/06009 428/458 |

(Continued)

OTHER PUBLICATIONS

Shuyi Li, et al Porous-wall hollow glass microspheres as novel potential nanocarriers for biomedical applications, Nanomedicine: Nanotechnology, Biology and Medicine, vol. 6, Issue 1, pp. 127-136, ISSN 1549-9634, (Year: 2010).*

(Continued)

*Primary Examiner* — Jennifer Wecker
*Assistant Examiner* — Jonathan Bortoli
(74) *Attorney, Agent, or Firm* — Goodhue, Coleman & Owens, P.C.

(57) ABSTRACT

An event detection composite in embodiments of the present invention may have one or more of the following features: (a) a plurality of solid and/or hollow and/or porous-wall microspheres, (b) a functional material disposed on or within the plurality of microspheres, wherein the functional material can have unique optical, electrical, magnetic, thermal, or chemical properties, where these properties can be realized upon the plurality of microspheres being exposed to a physical, optical, electrical, magnetic, thermal or chemical stimuli, and (c) a host matrix containing the plurality of microspheres.

7 Claims, 22 Drawing Sheets

(56) References Cited

U.S. PATENT DOCUMENTS

| | | | | |
|---|---|---|---|---|
| 2007/0190298 A1* | 8/2007 | Hampden-Smith | ..... | B42D 25/29 |
| | | | | 428/204 |
| 2008/0182056 A1* | 7/2008 | Bakker | ................ | A61K 9/5089 |
| | | | | 73/53.01 |
| 2011/0250626 A1* | 10/2011 | Williams | ................ | C12Q 1/61 |
| | | | | 106/4 |
| 2015/0056294 A1* | 2/2015 | Kaplan | ................... | A61P 25/28 |
| | | | | 514/662 |

OTHER PUBLICATIONS

Anderson and Weber "Fluorescence polarization of the complexes of 1-anilino-8-naphthalenesulfonate with bovine serum albumin. Evidence for preferential orientation of the ligand" Biochemistry, Aug. 1, 1969, 371-377 https://doi.org/10.1021/bi00829a051 (Year: 1969).*

Wicks et al. Glass microspheres hollow out a niche for anticounterfeiting strategies. (cover story). American Ceramic Society Bulletin, 95(6), 24-29. (Year: 2016).*

Meille et al Definitions of terms relating to crystalline polymers (IUPAC Recommendations 2011) (Year: 2011).*

* cited by examiner

STIMULI RESPONSIVE MICROSPHERE COMPOSITES

PRIORITY STATEMENT

This application claims priority to U.S. Provisional Patent Application No. 62/702,138, filed on Jul. 23, 2018, titled Stimuli Responsive Microsphere Composites all of which is hereby incorporated by reference in its entirety.

FIELD OF THE INVENTION

The present invention relates to microspheres. Particularly, the present invention relates to providing indicators of occurring events. More particularly, but not exclusively, the present invention relates to microspheres which respond to specific stimuli and cause a subsequent desired response.

BACKGROUND

The production of counterfeit goods is a growing problem in the United States (U.S.) and across the globe with significant detrimental impacts to the economy, consumer well-being, and national and international security. Counterfeiting impacts a variety of products including consumer goods, such as pharmaceutical drugs, and intermediate goods, such as microelectronics. Often, advanced functional materials with unique properties are incorporated into security features for product authentication. Unfortunately, counterfeiters have become increasingly sophisticated and are often able to duplicate and circumvent existing security features. Thus, there is a need for novel, functional materials to be incorporated into the next generation of security-end products.

Due to growing concerns of supply chains compromised by counterfeit products, security printing and other anti-counterfeiting strategies play increasingly important roles for a variety of industries. The impact of counterfeiting on legitimate economic activity is well-acknowledged. The total value of counterfeit and pirated goods is conservatively projected to rise from $923 billion in 2013 to $1.90 trillion in 2022. However, the effects of counterfeiting on national security and public safety are less recognized and perhaps more consequential than the known economic effects. As an example, the routine counterfeiting of electronic components can be considered, wherein the number of verified incidents quadrupled between 2009 and 2011. Of the millions of low-quality counterfeit components produced, some find their way into control systems used in military, aerospace, and medical applications where high reliability and performance are critical to successful operation. In these applications, a malfunction of a counterfeit component during operation could endanger many lives. Additionally, there are fears counterfeit components could act as "Trojan horses" which could be remotely disabled by malicious agents.

New security features allowing for improved detection and avoidance of counterfeit products are needed to prevent such outcomes. For example, it would be valuable to know if an event has occurred in which a security feature has been removed or modified.

Beyond anti-counterfeiting efforts, there are also many applications where it is important to identify excursions in specific environments. For example, it would be valuable to know if specific chemical species (e.g., pharmaceutical drugs), gases/vapors, radiation, and/or temperature fluctuations are introduced to a specific environment (e.g., a water supply).

Therefore, it would also be beneficial to have an improved detection method for most any material where the presence of the material would create an observable reaction. Thus, the reaction could alert the necessary personnel to remedy the situation, such as emergency responders.

It would also be beneficial to have smart composite containing materials which respond to specific stimuli and cause a subsequent desired response. These composites could be deployed to target detection of specific stimuli in a variety of environments. For example, it would be beneficial for polymer-based composite materials to exhibit self-healing functionality when damaged by mechanical shock caused by bullet penetration or other similar events.

SUMMARY

Therefore, it is a primary object, feature, or advantage of the present invention to improve over the state of the art.

An event detection composite in embodiments of the present invention may have one or more of the following features: (a) a plurality of solid and/or hollow and/or porous-wall microspheres, (b) a functional material disposed on or within the plurality of microspheres, wherein the functional material can have unique optical, electrical, magnetic, thermal, or chemical properties, where these properties can be realized upon the plurality of microspheres being exposed to a physical, optical, electrical, magnetic, thermal or chemical stimulus, and (c) a host matrix containing the plurality of microspheres.

An event detection system in embodiments of the present invention may have one or more of the following features: (a) a plurality of solid and/or hollow and/or porous-wall microspheres located within a host matrix, and (b) a functional material incorporated with the plurality of microspheres, wherein the functional material will provide a unique indicator if any of the microspheres are fractured exposing the functional material or activated by external stimulus.

A method for creating event detection composites in embodiments of the present invention may include one or more of the following steps: (a) providing a plurality of solid and/or hollow and/or porous-wall microspheres, (b) inserting a functional material having unique optical, electrical, magnetic, thermal, or chemical properties within the plurality of microspheres, wherein the functional material will provide a unique indicator if any of the microspheres are fractured exposing the functional material or activated by external stimulus, (c) adding the plurality of microspheres to a host matrix, (d) applying the host matrix to a product by aerosol jet deposition, (e) placing the plurality of microspheres in a solution of the functional material at ambient pressure, (f) evacuating ambient gasses, (g) transporting the solution through microsphere wall porosity, (h) loading additional solution upon restoration of ambient pressure; (i) coating the microspheres, and (j) providing controlled time release of materials loaded within the microspheres.

One or more of these and/or other objects, features, or advantages of the present invention will become apparent from the specification and claims follow. No single embodiment need provide every object, feature, or advantage. Different embodiments may have different objects, features, or advantages. Therefore, the present invention is not to be limited to or by any objects, features or advantages stated herein.

BRIEF DESCRIPTION OF THE DRAWINGS

Illustrated embodiments of the disclosure are described in detail below with reference to the attached drawing figures, which are incorporated by reference herein.

DETAILED DESCRIPTION

Figure 1:
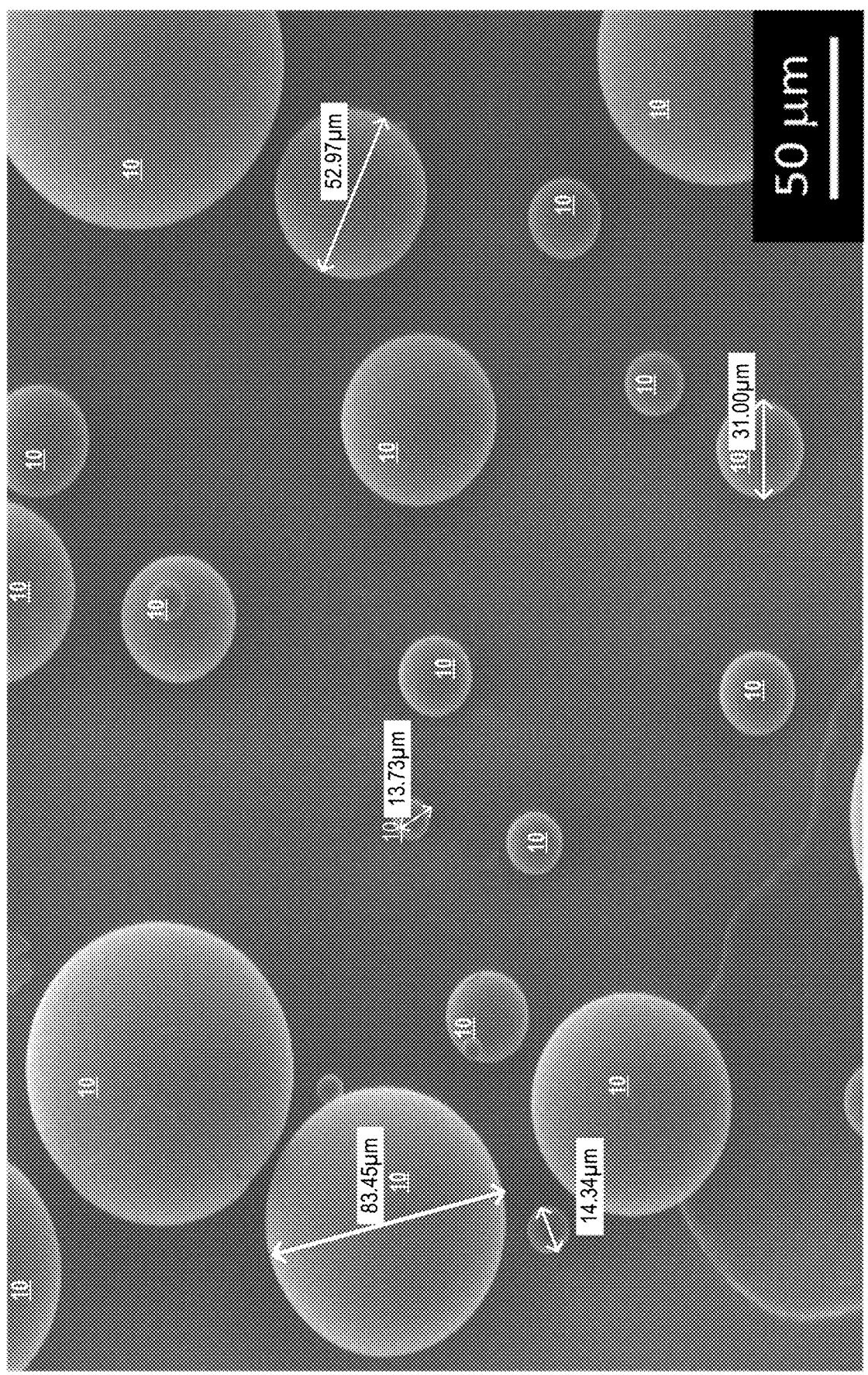
FIG. 1 is a scanning electron microscope (SEM) image showing multiple microspheres in accordance with an embodiment of the present invention.

The following discussion is presented to enable a person skilled in the art to make and use the present teachings. Various modifications to the illustrated embodiments will be clear to those skilled in the art, and the generic principles herein may be applied to other embodiments and applications without departing from the present teachings. Thus, the present teachings are not intended to be limited to embodiments shown but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the present teachings. Skilled artisans will recognize the examples provided herein have many useful alternatives and fall within the scope of the present teachings. While embodiments of the present invention are discussed in terms of stimuli-responsive composites, it is fully contemplated embodiments of the present invention could be used in most any specific stimuli event and subsequent desired response application without departing from the spirit of the invention.

While the detailed description is discussed in terms of the prevention of counterfeiting and security, there are a variety of applications where technology of embodiments of the present invention could be used outside of counterfeiting and security. For example, embodiments of the present invention could be extended to a smart composite containing microspheres responding to specific stimuli and causing a subsequent desired response, such as in pharmaceutical applications or energetics or chemical sensing. For example, they could be added to certain water supplies to release a conditioning element when the water chemistry exceeds specific conditions. Although specific examples of how the microspheres can be deployed are enumerated it is understood the deployment of microspheres is not limited or exclusive to the embodiments described. For example, aerosol jet printing is just one type of printing technology microspheres can be deployed in. The microspheres can also be deployed in a variety of liquid media or incorporated into composite or polymeric materials using a variety of manufacturing techniques. Similarly, negative pressure loading is but only one way amongst other methods used to load the microspheres.

One aspect to the development of more robust and effective security features is the incorporation of advanced functional materials with unique capabilities. One group of materials recently considered for these purposes are solid, hollow and porous-wall microspheres. The microspheres are real, silica microcapsules ranging in diameter from 10 to 100 μm and have shell walls with thicknesses of 1 to 3 μm. Although silica-rich microcapsules are described, the microspheres are not limited to silica as the microspheres can be constructed of other glass materials and the glass microspheres can take on the form of solid, hollow and/or the unique porous-wall microspheres. Within the thin walls of the microspheres, interconnected nanoscale porosity extends from the microsphere exterior to the interior, which allows the interior cavities to be filled with solid, liquid or gaseous cargos. By encapsulating functional materials (i.e., materials with unique optical, electrical, magnetic, thermal, or chemical properties) within microspheres, complex, hierarchical composites can be synthesized. These loaded microspheres can then be incorporated into security inks for printed security features on products and packaging, into matrix materials for functionalized casings and coatings, or into liquid products such as paints for covert taggants. While security ink is discussed through the specification, the inventors fully contemplate any host matrix which can hold, transport and/or provide a vehicle for the microspheres. The functional materials can also be incorporated in other ways such as in coatings on the glass microspheres.

The inventors have focused on the development of composite microspheres for printable security features sensitive to activation via mechanical tampering (e.g., grinding or abrasion) and methods often employed by counterfeiters when remarking outdated components (e.g., electronic components). Further, the inventors propose a smart composite containing microspheres responding to specific stimuli and causing a subsequent desired response. Example applications include pharmaceuticals or energetics or chemical sensing or self-healing materials. Further, embodiments of the present invention could be added to certain water supplies to release a conditioning element when the water chemistry exceeds specific conditions.

With reference to FIG. 1 a scanning electron microscope (SEM) image showing multiple microspheres in accordance with an embodiment of the present invention is shown. Here, the inventors present an approach to the development of composite microspheres 10 for applications using solutions containing molecules or solutes with dimensions in the sub-nanometer range, which are expected to diffuse through the wall porosity more effectively than dispersions of pre-synthesized nanoparticles. These solutions may serve as precursor functional materials, functional materials and/or reactive functional materials depending on the desired end-product. Embodiments of the present invention show the feasibility of synthesizing composite microspheres containing cargo through development of suitable processing procedures and characterization techniques.

Embodiments of the present invention involve the use of microspheres 10 as carriers for functional materials having unique chemical, thermal, mechanical, optical, electrical or magnetic properties for use in product security, authentication and/or anti-counterfeiting applications. Microspheres 10 are small hollow spheres, roughly 20-40 micrometers in size.

Figure 2:
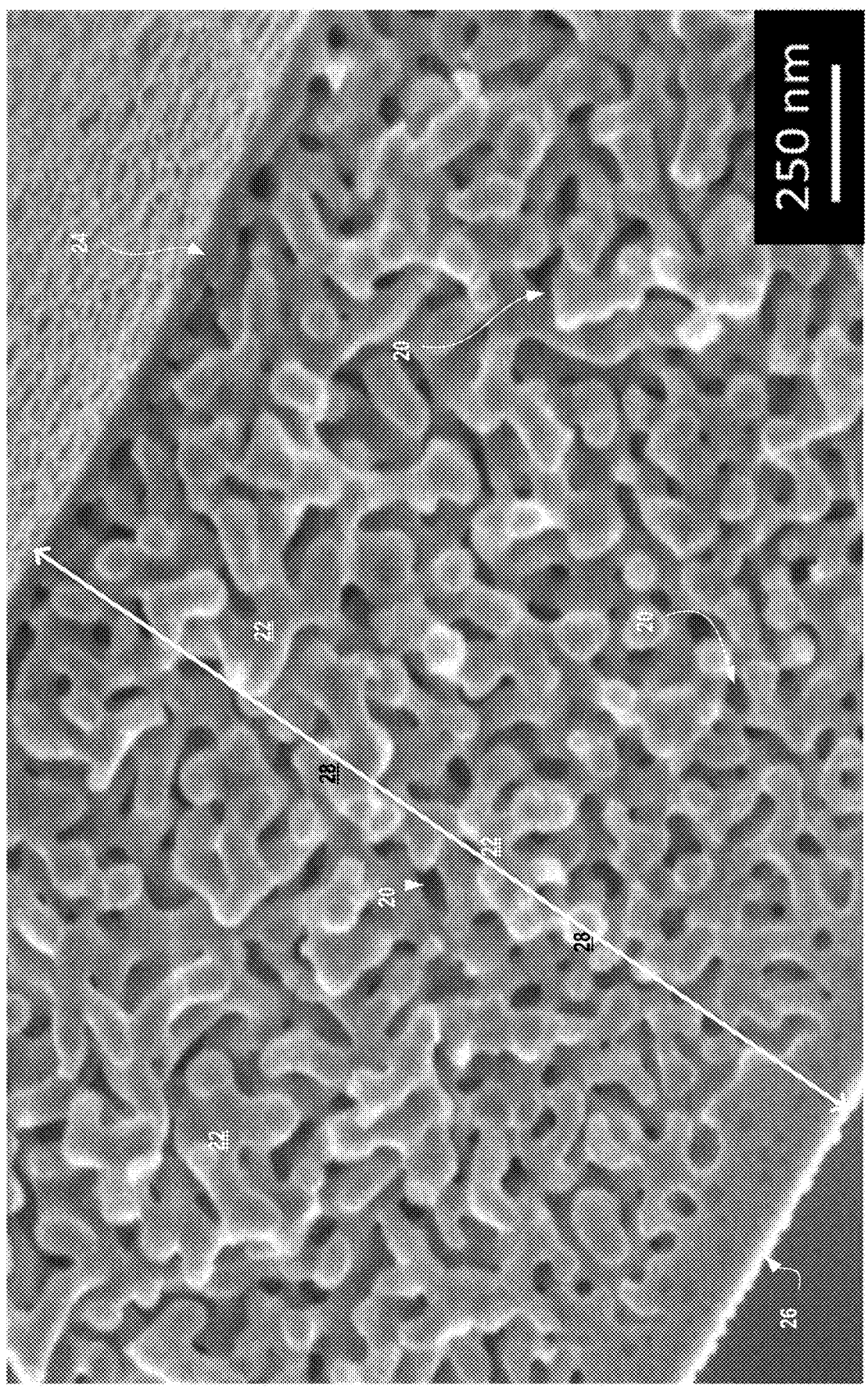
FIG. 2 is a SEM image revealing the wall cross-section of a microsphere in accordance with an embodiment of the present invention.

With reference to FIG. 2 a SEM image revealing the wall cross-section of a microsphere in accordance with an embodiment of the present invention is shown. A unique feature of these microspheres 10 is their thin (1000-3000 nm) walls 28 and small (10-100 nm) interconnected wall porosity 20 which travels from the outside of the sphere wall 26 (or shell) to the inside 24. The presence of these pores 20 allows the microspheres 10 to be loaded with gases, liquids and solids. An aspect of embodiments of the present invention are the use of these microspheres 10 for security and anti-counterfeiting applications.

Embodiments of the present invention include compositions of microspheres 10 and functional materials (e.g., gases, liquids, solids) with unique properties (e.g., chemical, thermal, mechanical, optical, electrical, magnetic), wherein one or more functional materials are positioned within the microsphere 10, and the use of such compositions for security, marking or anti-counterfeiting applications.

Embodiments of the present invention involve the use of microspheres, including microspheres 10 for the development of "smart" composite systems. Composite systems will include: (1) a matrix material including liquid (e.g., ink), paste, and/or solid material (e.g. polymer, ceramic or metallic material), (2) microspheres 10 including porous wall hollow microspheres 10, and (3) functional material contained on or within the microspheres 10 having unique chemical, thermal, mechanical, optical, electrical or magnetic properties.

Porous-wall hollow microspheres 10 are small hollow spheres, roughly 20-40 μm in size. A unique feature of these spheres is their small (10-100 nm) interconnected wall porosity traveling from the outside of the sphere wall 26 (or shell) to the inside 24. The presence of these pores 20 allows the microspheres 10 to be loaded with gases, liquids, and solids. Thus, specific functional material can be loaded within the microspheres 10 to elicit a specific response. For example, a composite can be developed containing microspheres 10 loaded with chemical A and a separate set of microspheres 10 loaded with chemical B. Under a desired stimulus (e.g., photoactivation, mechanical abrasion, or stress) the microspheres 10 could then release the chemicals (either by fracturing the spheres or releasing the payload through the wall porosity) so chemicals A and B undergo subsequent chemical reaction. This reaction may then be detected by a variety of means. Thus, the system can be used for a variety of sensing applications or possibly as an anti-tampering device.

Embodiments of the present invention provide new developments of smart composites. A feature of embodiments of the present invention is the microspheres 10 can be loaded with a wide array of functional materials. Furthermore, the deployment of the microspheres 10 can be controlled by using external coatings (on the microsphere 10) or controlling the mechanical properties (i.e., strength, toughness) of the microspheres 10. Finally, considering the base material of the microsphere 10 can be a silicon-based glass the microspheres 10 themselves are stable in a wide variety of environments including aggressive chemical environments and moderately high temperatures. This makes the materials flexible for incorporation in a host of manufacturing processes and external environments.

Microspheres 10 are a unique material with many potentials in security technology. Embodiments of the present invention focus on the development of host matrices containing microspheres 10, whereby the microspheres 10 serve as storage vessels for a variety of functional materials. One embodiment of the present invention discloses aerosol jet deposition of hollow glass microspheres 10 onto a substrate. Another embodiment of the present invention discloses loading of microspheres 10 with gold nanoparticles. Both embodiments demonstrate the development of a host matrix utilizing microspheres 10 loaded with functional materials.

The inventors have developed a host matrix containing microspheres 10 loaded with one or more functional materials (e.g. materials with unique optical, electrical, magnetic, thermal, or chemical properties). The microsphere-based host matrix could be used to fabricate next-generation security devices with direct write printing technology. Encapsulating various payloads within microspheres 10 would allow for an efficient deposition process utilizing the same printing parameters for a variety of functional materials. Thus, a variety of functional host matrices may be developed and deployed within a single technology envelope. Additionally, the encapsulation of functional materials within thin glass walls 28 can be exploited to create security features for use in anti-tamper applications.

As first steps in developing a host matrix incorporating functionally loaded microspheres 10, two feasibility studies were performed. One study sought to demonstrate microspheres 10 could survive a printing process using an aerosol jet deposition system. The second study focused on demonstrating the feasibility of loading microspheres 10 with metallic nanoparticles through the wall porosity.

Inks containing microspheres 10 were developed. The chemical, mechanical, and rheological properties of the ink, suitable for the specific direct write technology utilized for the printing process, were identified. Additionally, parameters involved in the printing process were optimized to ensure successful deposition of the microspheres 10 onto a substrate.

An ink consisting of 5.0 wt % (weight by percentage) polyvinylpyrrolidone (PVP) and 0.2 wt % 3M™ iM30K Glass Bubbles (average diameter of 18 µm) in ethylene glycol was developed for aerosol jet deposition by a Sonotek ExactaCoat SC system. The loading of the ink with both the microspheres 10 and the PVP, which was used for adhesion of the microspheres 10 to the substrate following printing, was restricted by the printing system's rheological limitations, which were experimentally determined. Ethylene glycol's viscous nature helped to slow the microspheres' tendency to float to the surface of the ink. Dispersion of the microspheres in the ink was maintained enough to allow for generation of an aerosol spray.

The ink containing the iM30K Glass Bubbles was printed onto glass and paper substrates. Printing parameters such as volumetric infusion rate and line spacing were experimentally optimized to eliminate overspray of the ink and infusion line blockage caused by microsphere buildup.

Figure 3:
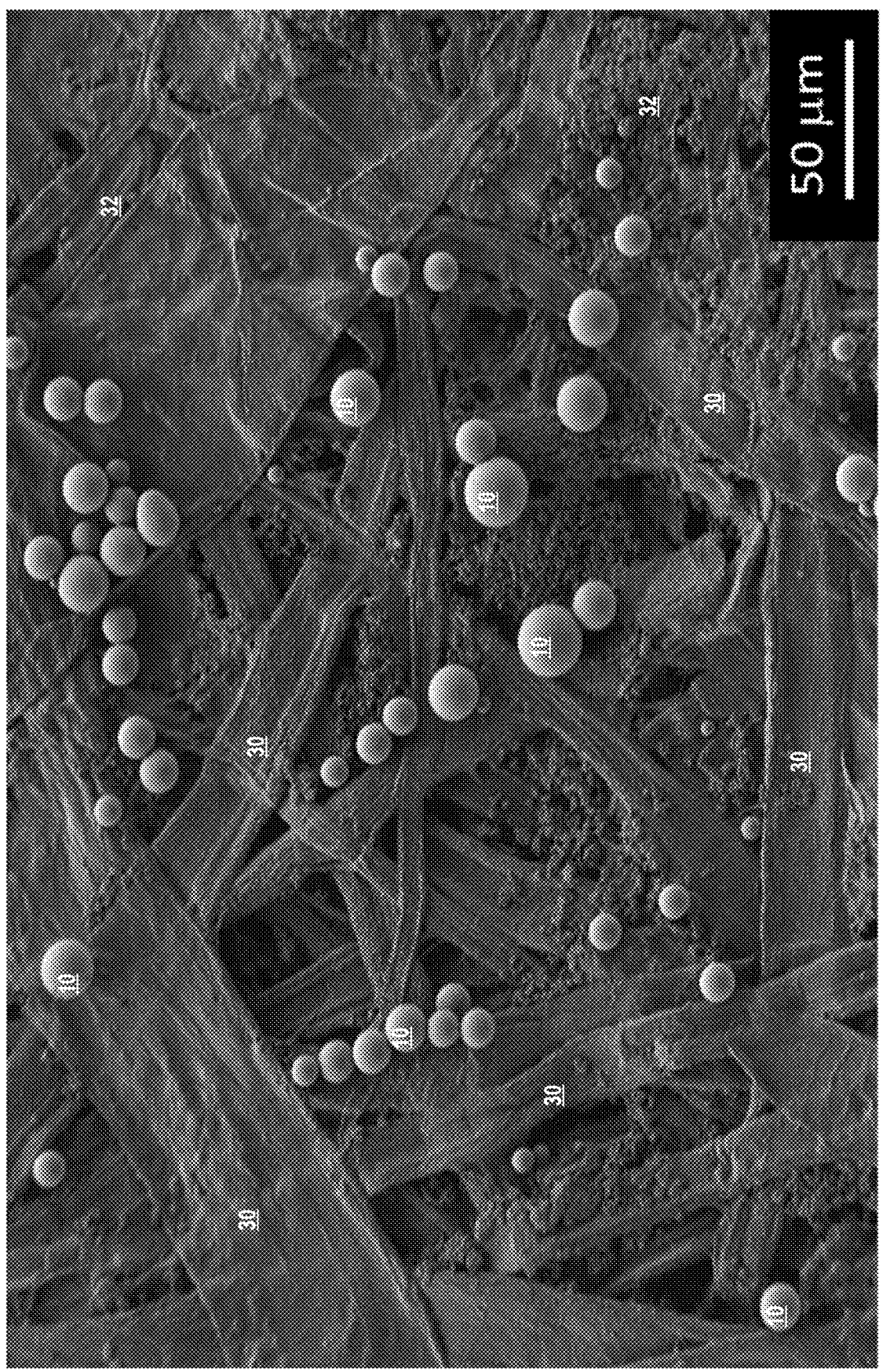
FIG. 3 is a SEM image showing the result of the process of aerosol jet deposition of iM30K Glass Bubbles with PVP onto copy paper in accordance with an embodiment of the present invention.

With reference to FIG. 3 a SEM image showing aerosol jet deposition of iM30K Glass Bubbles with PVP onto copy paper in accordance with an embodiment of the present invention is shown. The iM30K Glass Bubbles were successfully deposited onto glass and paper substrates. FIG. 3 shows SEM micrographs of iM30K Glass Bubbles with PVP printed onto copy paper 32 using an aerosol jet deposition system. From inspection of FIG. 3, it is clear the microspheres 10 remain intact after printing with limited signs of microsphere fracture. Also, it is noted the microspheres 10 appear aligned with the paper fibers 30, potentially caused by evaporative assembly.

Figure 4:
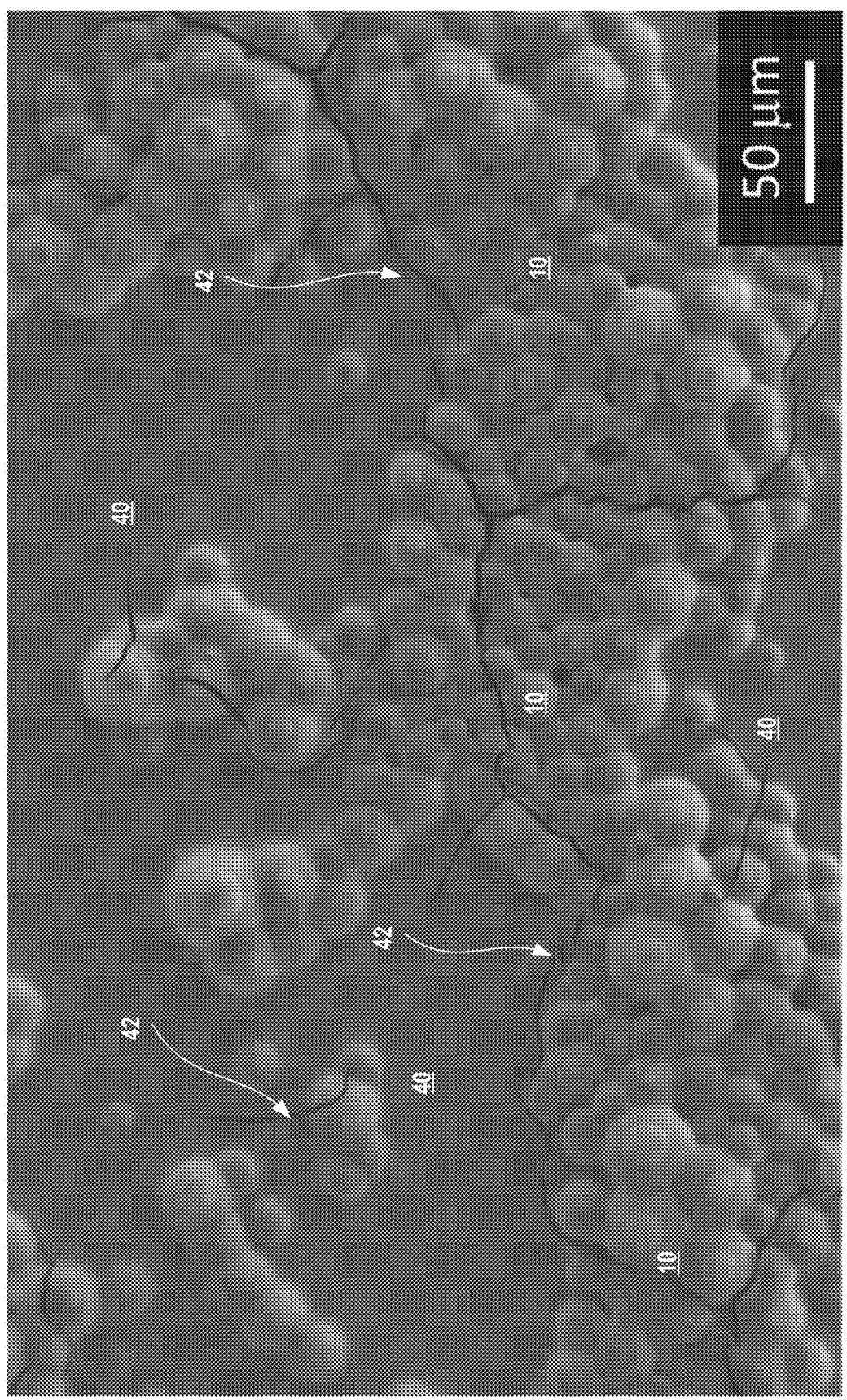
FIG. 4 is a SEM image showing the result of the process of aerosol jet deposition of iM30K Glass Bubbles with PVP onto a glass slide in accordance with an embodiment of the present invention.

With reference to FIG. 4 a SEM image showing aerosol jet deposition of iM30K Glass Bubbles with PVP onto a glass slide in accordance with an embodiment of the present invention is shown. FIG. 4 shows the same ink printed on a glass substrate 40. The image was captured near the edge of the printed area and partially depicts a ring of microspheres 10 believed to have formed during drying due to the coffee ring effect. In physics, a "coffee ring" is a pattern left by a puddle of particle-laden liquid after it evaporates. The phenomenon is named for the characteristic ring-like deposit along the perimeter of a spill of coffee. The mechanism behind the formation of these and similar rings is known as the coffee ring effect or in some instances, the coffee stain effect or simply ring stain. From inspection of FIG. 4, cracks 42 which formed during the drying process are present in the film. These results demonstrated, with the proper ink characteristics and printing parameters, hollow glass microspheres 10 can be printed using an aerosol jet deposition system.

With reference again to FIG. 3, there is a non-uniform coverage of the paper substrate 32 after printing. Additionally, the coffee ring effect, which occurred after printing on glass substrates 40 (FIG. 4), can be minimized using binary solvents.

The process used to develop the ink which resulted in the successful aerosol jet deposition of these microspheres 10 can be extended in the development of inks containing microspheres 10. It should be noted, however, the iM30K Glass Bubbles used in this feasibility study are both relatively small and very strong. Microspheres 10, porous-wall microspheres specifically, on the other hand, will be weaker due to the induced wall porosity.

Figures 5A, 5B, 5C, 5D:
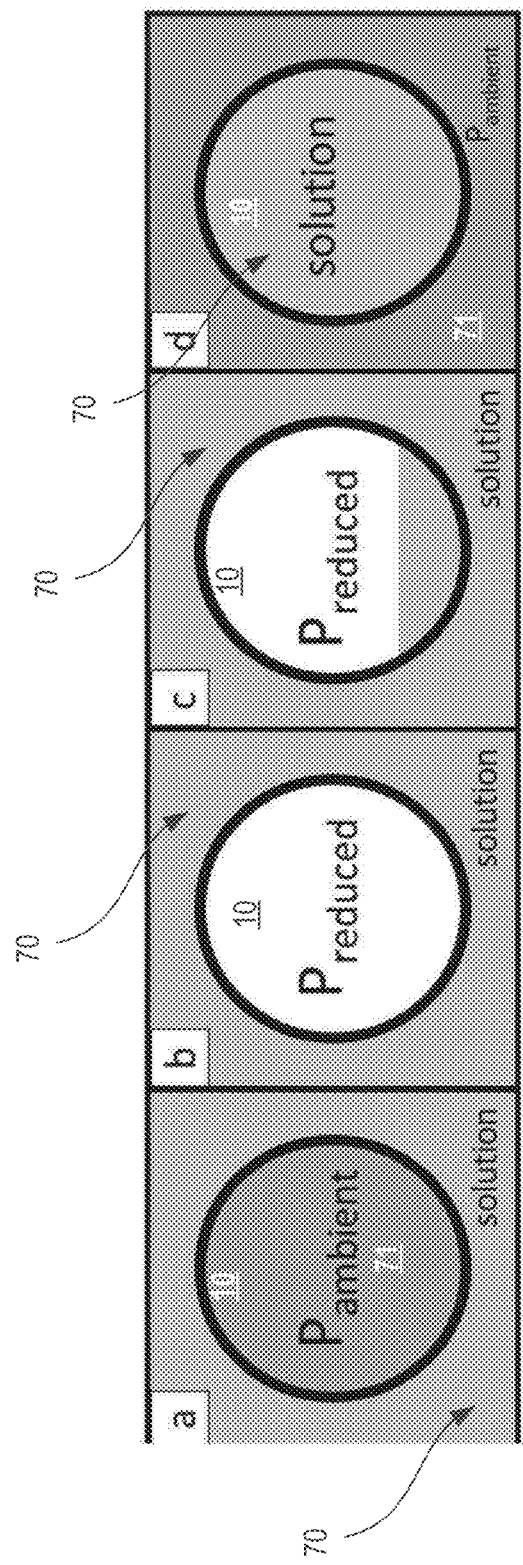
FIGS. 5a-d are a pictorial illustration of a microsphere wet vacuum loading process in accordance with an embodiment of the present invention.

With reference to FIGS. 5a-d a pictorial illustration of a microsphere wet vacuum loading process in accordance with an embodiment of the present invention is shown. A wet vacuum process, based on techniques developed for hydrogen-storage applications, was used to load microspheres 10. In FIG. 5a, a microsphere 10 is dispersed in solution 70 at ambient pressure. In FIG. 5b, evacuation of ambient gasses 71 is occurring. In FIG. 5c, partial transport of solution 70 through microsphere wall porosity is occurring. In FIG. 5d, loading of additional solution 70 upon restoration of ambient pressure 71 is occurring. The loading of porous structures with liquids is often a diffusional process. When the porosity of the structure has nanoscale dimensions and contains entrapped air, the diffusion process may take weeks to complete. Wet vacuum techniques may be used to increase the loading kinetics by removing entrapped air (to the extent possible) and encouraging liquid diffusion by imposing a pressure differential.

Initially, dry microspheres 10 are dispersed in solution through gentle mixing (FIG. 5a). The microspheres 10 contain air at ambient pressure 71 and will typically float in a solution 70. To partially remove the entrapped air present within the pores and interior cavity of the microspheres 10, the dispersion is placed within a desiccator chamber and a rotary vane vacuum pump is used to reduce the pressure within the chamber. The partial removal of air from the interior of the microspheres 10 (FIG. 5b) may initiate solution transport through the wall porosity (FIG. 5c). After a prescribed soaking duration, the chamber is vented to ambient pressure 71. The pressure difference between the microsphere interiors and the external environment drives diffusion of the solution into the interior cavity (FIG. 5d). The evacuation and venting process (FIGS. 5b-d) may be cycled until a suitable number of microspheres 10 sink in a solution 70, a signal the solution 70 has displaced a significant volume of entrapped air within the microspheres 10. Cycling of the evacuation and venting steps is often required due to variation in wall porosity and contact with solution 70 amongst microspheres 10.

Certain wet vacuum loading parameters may be varied depending on properties of the loading solution 70 (e.g., viscosity, solute size, and vapor pressure). In this work, the variable parameters were the magnitude of reduced pressure, the soak time at reduced pressure, and the number of evacuation/vent cycles. Additional steps not included in the general wet vacuum loading procedure were also incorporated for some material systems. These case specific details will be discussed below in their respective sections.

As mentioned, microspheres 10 have been loaded with a wide range of materials for a variety of applications. One embodiment can load microspheres 10 with metallic nanoparticles with properties applicable to security printing, such as unique optical, electrical, magnetic, thermal, or chemical properties. Loading microspheres 10 with gold nanoparticles is one embodiment for the loading of microspheres 10 with functional nanoparticles.

Microspheres 10, with an average diameter of about 27 microns, were soaked in an approximately 18 nanomolar citrate-capped gold nanoparticle aqueous dispersion. Pressure and heat were used to impregnate the microspheres 10 with the 12-15 nm spherical gold particles. Multiple loading cycles were performed, and, after each cycle, the microspheres 10 were washed and dried to gradually build up the amount of gold on the interior of the microspheres 10.

The loaded microspheres 10 were then fractured and characterized using SEM and energy dispersive X-ray spectroscopy (EDS).

Figure 6:
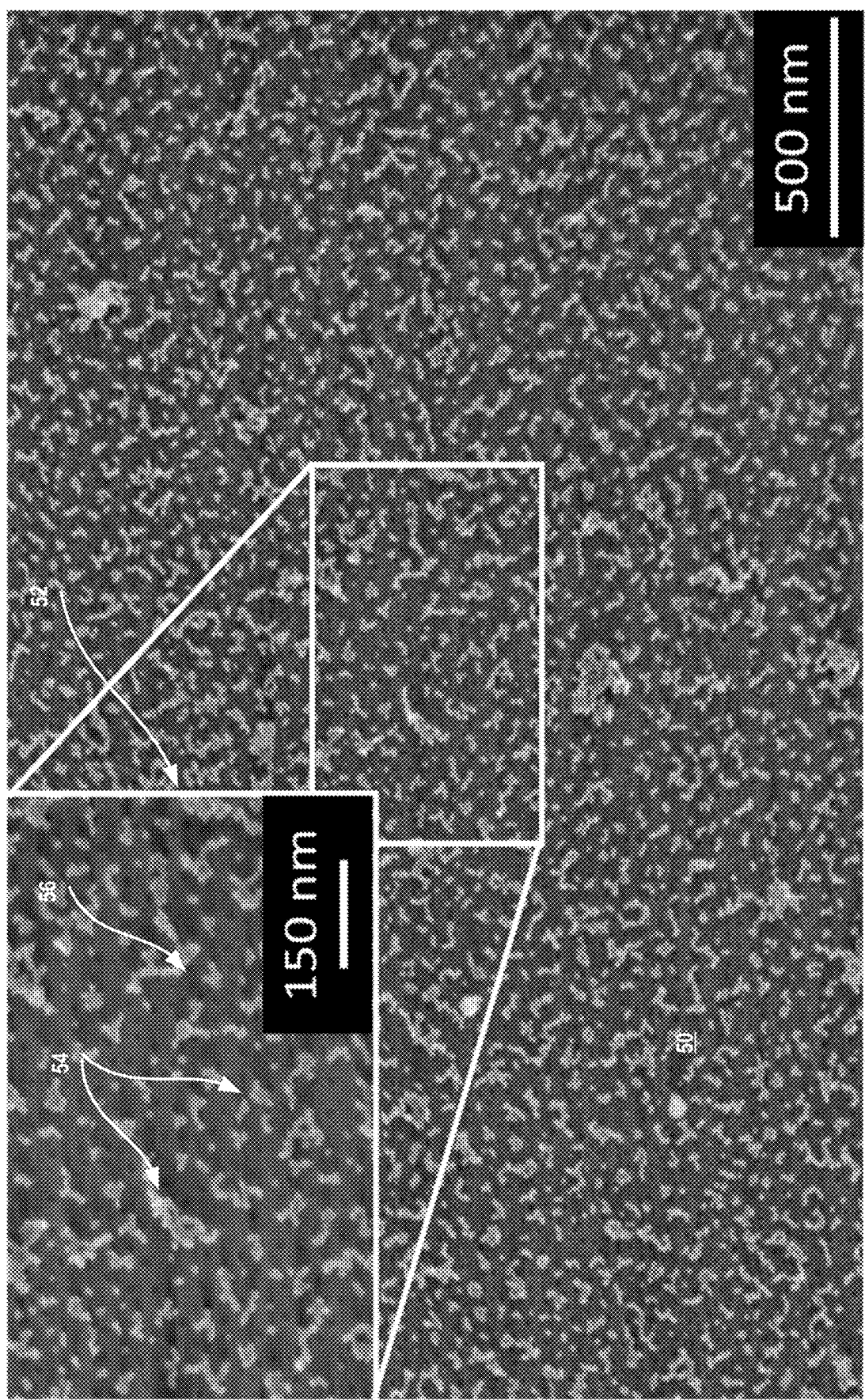
FIG. 6 is a SEM image of the interior wall surface of a microsphere after loading the sphere with gold nanoparticles in accordance with an embodiment of the present invention.

With reference to FIG. 6 a SEM image of the interior wall surface of a microsphere after loading the sphere with gold nanoparticles in accordance with an embodiment of the present invention is shown. Gold nanoparticles 54 were found on the wall interior 28 and inside the wall porosity of a microsphere 10 cracked open for characterization. FIG. 6 shows a SEM image of the interior surface 50 of a microsphere 10 after completion of the loading process. The inset 52 depicts a higher resolution image where the gold nanoparticles 54 (light regions) and wall porosity 56 (dark circular openings) are clearly visible. Note, this sphere was deliberately fractured to inspect the internal surface. Clearly, gold nanoparticles 54 (light regions), present in both clusters and as individual particles, were found uniformly distributed on the interior microsphere surface. From inspection of the inset 52 in FIG. 6, the wall porosity 56 (dark circles) can also be observed. The individual spherical nanoparticles are indeed about 12-15 nm in diameter and the pore openings in this area are roughly 12-20 nm in diameter.

Figure 7:
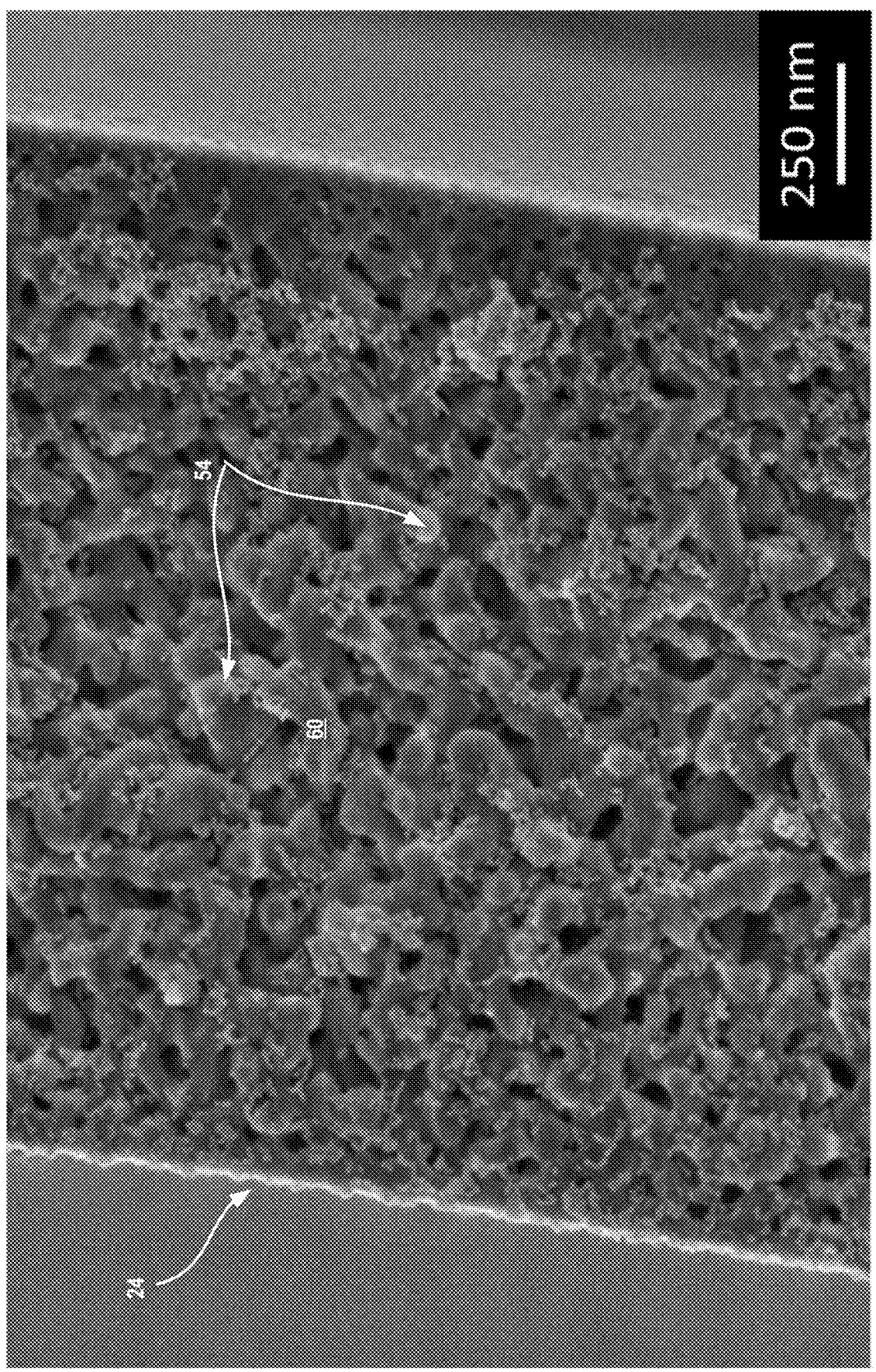
FIG. 7 is a SEM image showing the microsphere wall cross-section after loading the sphere with gold nanoparticles in accordance with an embodiment of the present invention.

With reference to FIG. 7 a SEM image showing the microsphere wall cross-section after loading the sphere with gold nanoparticles in accordance with an embodiment of the present invention is shown. An SEM image revealing the wall cross-section 60 of a microsphere 10 after completion of the loading process and the deliberate fracture of the sphere. Gold nanoparticles 54 are present as light-colored spheres and clustered spheres in this FIG. From inspection of FIG. 7, and comparison with FIG. 2 (unloaded sphere wall 32 cross-section), the wall cross-section 60 contains a significant coverage of gold nanoparticles 54 (light regions). Also, the pores 20 in this area are about 50-90 nm at their widest points. The presence of gold nanoparticles 54 on the interior wall surface 24 and within the microsphere's internal wall porosity strongly suggests nanoparticles traveled through the porosity and loaded the microsphere 10. The microsphere 10 had undergone five separate loading cycles, all of which utilized both pressure and elevated temperatures, and soaking times ranging from 30 minutes to 2 hours.

The discovery of gold nanoparticles 54 on the interior wall surface 24 and within the wall porosity of a microsphere 10 demonstrated the loading of microspheres 10 with metallic nanoparticles is indeed feasible. These results provide methods developed to load microspheres 10 with nanoparticles functionalized for security printing applications.

The inventors have demonstrated the ability to print microspheres, albeit small and very strong microspheres, with an aerosol jet deposition system and the ability to load microspheres 10 with gold nanoparticles 54. The inventors fully contemplate incorporating microspheres 10 into host matrices. Other embodiments disclose loading microspheres 10 with a variety of functional materials, including metallic nanoparticles (FIG. 21), and an ink containing these loaded microspheres 10 for use in aerosol jet deposition systems. Such a novel ink would have many applications in new generations of security features.

Microspheres 10 with an average diameter of 26 μm were obtained from the Applied Research Center of Aiken, SC. The discussion below describes the motivation, loading process, and characterization of composites fabricated by combining these microspheres 10 with functional payload materials.

Figure 8:
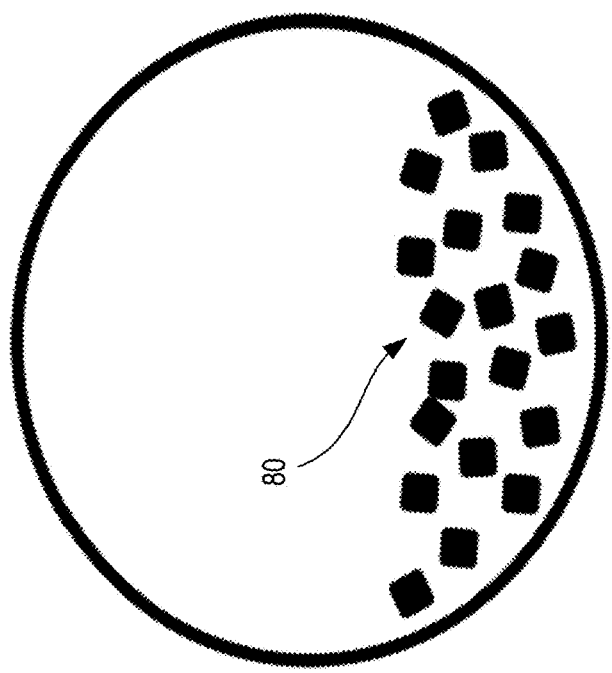
FIG. 8 is a pictorial illustration of loaded precursor solutions converting to functional solid materials within microspheres in accordance with an embodiment of the present invention.
Figure 8:
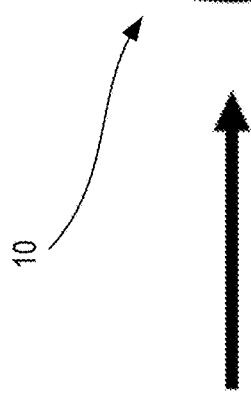
Figure 8:
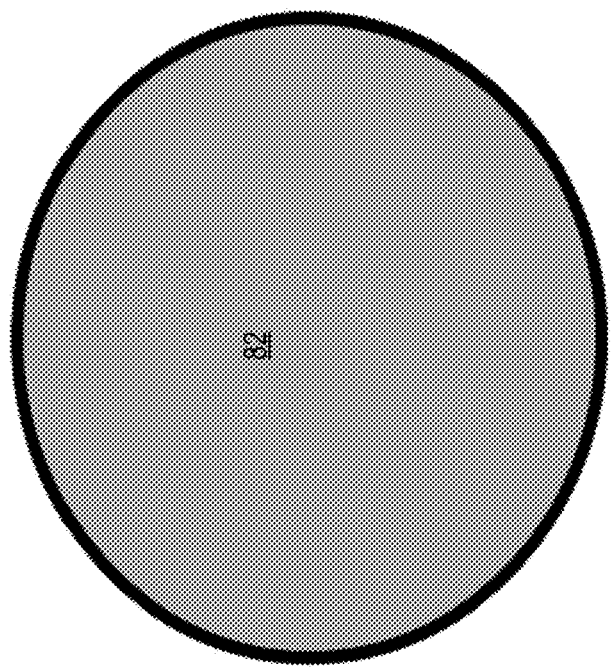

With reference to FIG. 8 a pictorial illustration of loaded precursor solutions converting to functional solid materials within microspheres in accordance with an embodiment of the present invention is shown. The use of nanoparticles in security printing is possible due to their exceptional, functional responses to a variety of external stimuli used during product authentication. Encapsulation of these materials by microspheres 10 could provide enhanced functionalities. Moreover, while direct loading of nanoparticle dispersions via wet vacuum techniques is feasible, the process yield (or loading factor) is limited which may limit performance/functionality. Solution based synthesis of functional solids presents a more feasible method of loading microspheres 10. Precursor materials are more easily transported through the wall porosity and the desired payload can be synthesized on the interior of the microsphere 10 (FIG. 8). There exists a wide variety of solution-based synthesis methods (e.g., thermal activation, chemical precipitation) for producing various functional solids meaning numerous types of composite microspheres could be fabricated and deployed in security devices. For all these potential material systems, the encapsulation of the functional material adds security in a stimulus, such as mechanical abrasion, is required to release the payload material to allow for its detection during product authentication.

For process development and demonstration of feasibility, the synthesis of cupric oxide (CuO) structures 80 within microspheres 10 from thermal treatments of loaded aqueous copper (II) chloride ($CuCl_2$) solution was performed. The precursor solution was made by dissolving copper (II) chloride dihydrate ($CuCl_2.2H_2O$) in deionized (DI) water to form a 1M aqueous solution. This solution was loaded into microspheres 10 at room temperature using the wet vacuum process described previously. The reduced pressure was 30 kPa below ambient pressure and the soak duration was 0.5 h. Three evacuation/vent cycles were performed after which the microspheres 10 were rinsed and filtered with deionized water using a standard vacuum filtration setup. The $CuCl_2$-loaded microspheres 82 were heated in an air furnace by ramping the temperature from room temperature to 450° C. at 2° C./min, followed by a 3 h hold at 450° C. Samples were then cooled to room temperature in the furnace.

Figure 9:
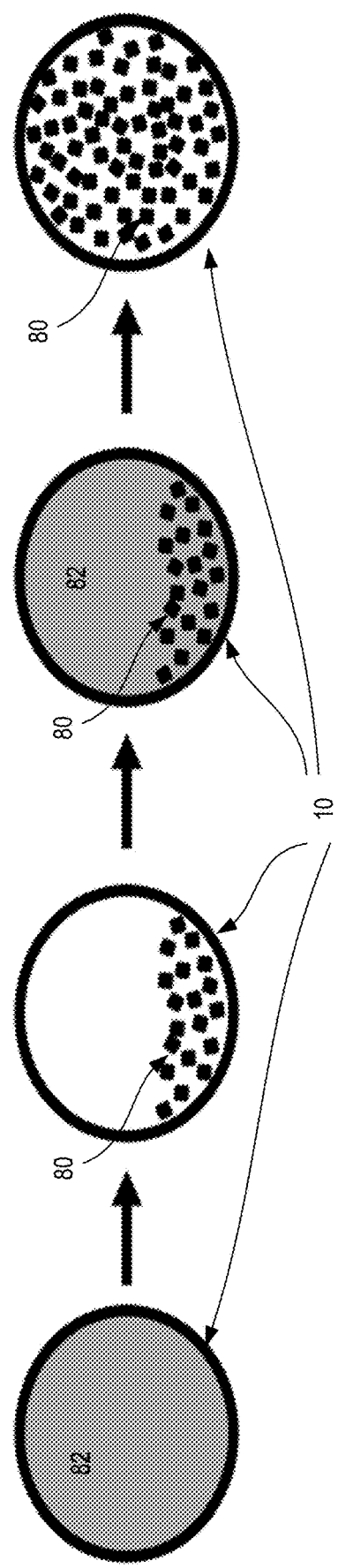
FIG. 9 is a pictorial illustration of increasing the load factor by repeating in situ synthesis steps until microspheres are filled with payload material in accordance with an embodiment of the present invention.

With reference to FIG. 9 a pictorial illustration of increasing the load factor by repeating in situ synthesis steps until microspheres are filled with payload material in accordance with an embodiment of the present invention is shown. For some samples, additional processing steps were taken to maximize the load factor (i.e., payload volume:microsphere volume) of microspheres 10. The entire in situ CuO synthesis, from wet vacuum loading to thermal treatment, was repeated twice to build up the amount of payload within the microspheres 10. The same wet vacuum and heat treatment parameters were utilized for both loading cycles. Intermediate wash stages were also incorporated to the loading process due to past observations of solid payload formation within wall pores and on the microsphere exterior surfaces. These observations suggested the wet vacuum loading process may be hindered during repeated cycles due to pore blockage. Thus, after the first loading cycle, microspheres 10 were soaked in 0.5M hydrochloric acid (HCl) for 10 min to dissolve undesired CuO 80 present on the exterior surface or within the wall porosity of the microspheres 10. After this wash step, the final loading cycle was conducted. The repeated loading and acid washing process did not achieve the desired load factor portrayed in FIG. 9.

Figure 22:
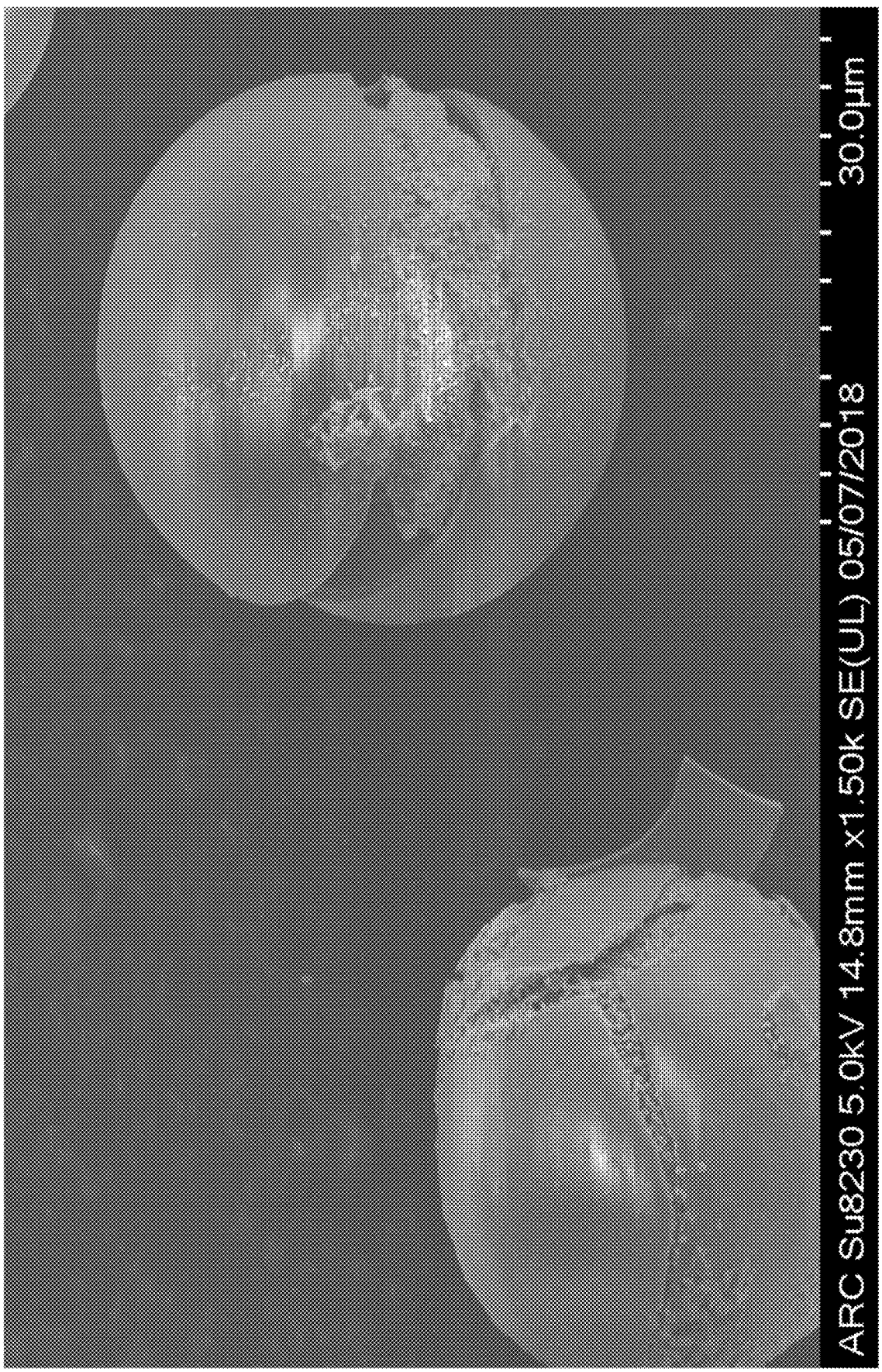
FIG. 22 is a SEM image of a porous-wall hollow glass microsphere filled with $CuCl_2$ to the extent the microspheres broke in embodiments of the present invention Some of the figures include graphical and ornamental elements. It is to be understood the illustrative embodiments contemplate all permutations and combinations of the various graphical elements set forth in the figures thereof.

Rather than increasing the number of CuO structures 140, the size of the structures increased. This was likely caused by preferential dissolution of small CuO crystals during the acid wash followed by preferential nucleation and growth at the undissolved, larger CuO structures 140 during the next loading cycle. Thus, the number of initial CuO structures 140 may dictate the maximum attainable number of distinct structures regardless of the number of loading cycles. Perhaps, if the acid wash is less severe, complete dissolution of small CuO structures 140 can be prevented and the initial number of CuO structures 140 can be grown to occupy the total interior volume of the microspheres 10. To fill the interior with a greater number of small structures, as might be desired for tamper-activated security features, different heating ramps or precursor concentrations should be investigated, in addition to chemical precipitation methods, to determine if the nucleation and growth of the CuO structures 140 can be better controlled. In addition, the size and morphology of the through-wall porosity of the microspheres 10 could be tailored to increase the loading factor. For example, FIG. 22 shows an SEM image of a porous-wall hollow glass microsphere that has been filled with $CuCl_2$ to the extent that the microspheres broke in embodiments of the present invention. This was carried out by increasing the size of the through-wall porosity.

Loaded microspheres 10 were characterized using SEM, EDS, and x-ray diffraction (XRD). The interiors of the loaded microspheres 10 were analyzed using SEM by intentionally fracturing microspheres to expose their interior surfaces. EDS and XRD were used to identify the chemical composition and structure of the payload material. Comparisons were made between the microspheres 10 loaded and heat treated once and the microspheres 10 loaded and heat treated twice with an intermediate acid wash.

Figures 10A, 10B:
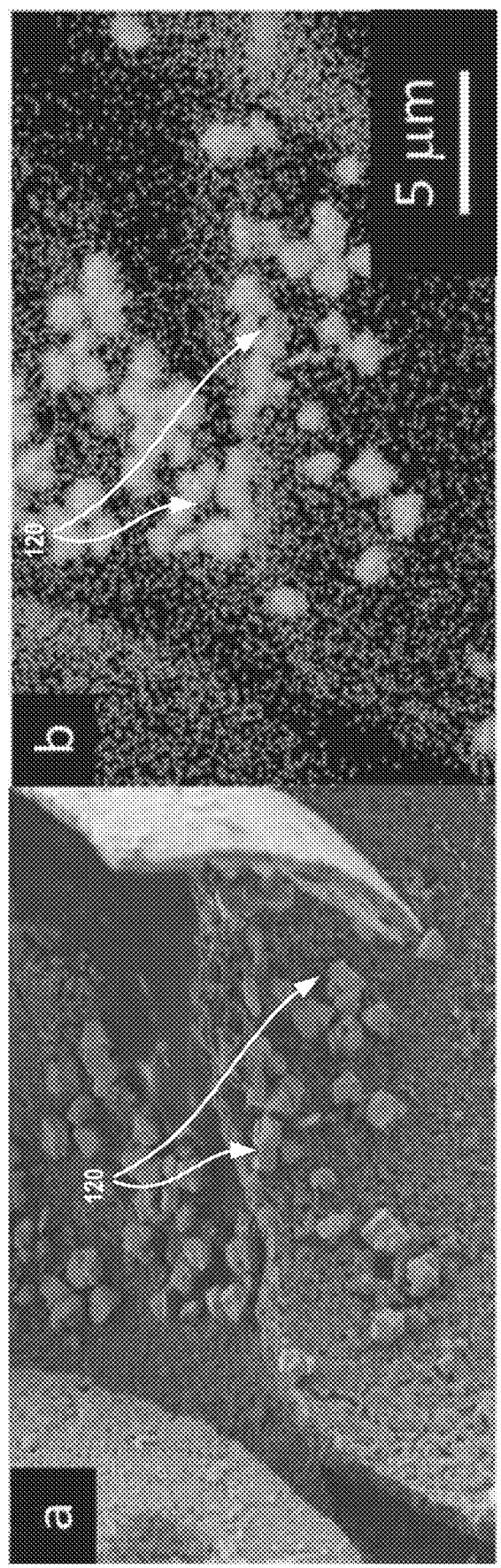
FIG. 10a is a SEM image depicting block-like CuO structures on the interior surface of a microsphere in accordance with an embodiment of the present invention.
FIG. 10b is an energy dispersive x-ray spectroscopy (EDS) copper elemental map of the same area of the microsphere interior shown in 12a in accordance with an embodiment of the present invention.

With reference to FIG. 10*a* a SEM secondary electron image depicting block-like structures on the interior surface of a microsphere in accordance with an embodiment of the present invention is shown. Characterization of the $CuCl_2$-loaded 82 and heat-treated microspheres revealed CuO microcrystals 80 were synthesized on the interior of the microspheres 10. FIG. 10*a* is an SEM image of the interior surface of a microsphere 10 intentionally fractured for inspection of its payload. The microsphere 10 was confirmed by SEM to be intact prior to intentional fracture. Numerous block-like structures 120 can be observed on the interior surface of the microsphere 10. EDS analysis determined the chemical composition of the structures consisted primarily of copper and oxygen.

With reference to FIG. 10*b* an EDS copper elemental map of the same area of the microsphere interior shown in FIG. 10*a* in accordance with an embodiment of the present invention is shown. Further, the EDS elemental map (FIG. 10*b*) shows a clear correlation between the block-like structures 120 and copper-concentrated regions. Similar observations were made for numerous microspheres 10 fractured for inspection, demonstrating the effectiveness of loading solutions rather than pre-synthesized solids. The SEM/EDS results provide strong indication copper oxide structures were synthesized in situ as intended. It could not be determined from this analysis, however, if the structures were CuO, as desired, or another oxide stoichiometry such as $Cu_2O$.

Figure 11:
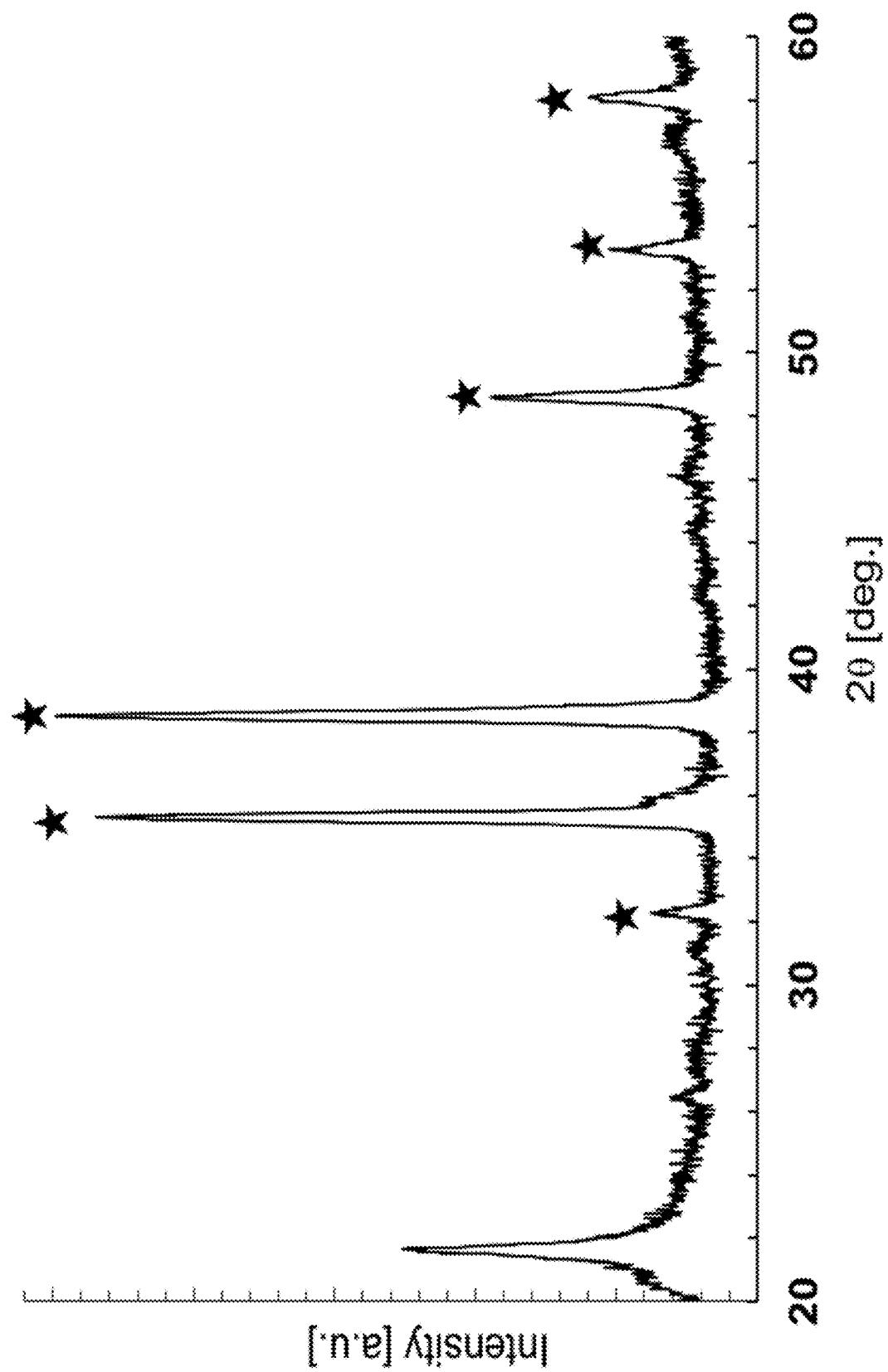
FIG. 11 is an x-ray diffraction (XRD) pattern of CuO-loaded microspheres in accordance with an embodiment of the present invention.

With reference to FIG. 11 an XRD pattern of CuO-loaded microspheres in accordance with an embodiment of the present invention is shown. XRD was used to determine the copper oxide phase. FIG. 11 provides an XRD pattern for microspheres 10 following a single loading. The peaks identified with a star in FIG. 11 are peaks confirmed to correspond to copper (II) oxide (CuO) based on comparison with a CuO powder XRD standard.

The combination of the SEM, EDS, and XRD results confirms the identity of the structures as crystalline CuO. While the desired chemical composition was obtained, the size and morphology of the acquired payload limits the optical functionality of this system. Most reports of CuO luminescence are unsurprisingly related to nanostructures rather than microstructures. As the synthesis method used does not permit explicit control of the size and morphology of the product, alternative synthesis methods, such as chemical precipitation of cupric salt by alkaline solutions, may be required to control the growth of CuO. From inspection of FIG. 10*a*, the CuO load factor, after one loading/conversion cycle, is quite small. Considering the limited CuO coverage observed on the surface of the fractured microsphere, it is clear a significant number of additional loading cycles would be required to fill the interior volume of the microspheres. These observations justify the investigation into the effects of multiple loading cycles on CuO load factor.

Figures 12A, 12B:
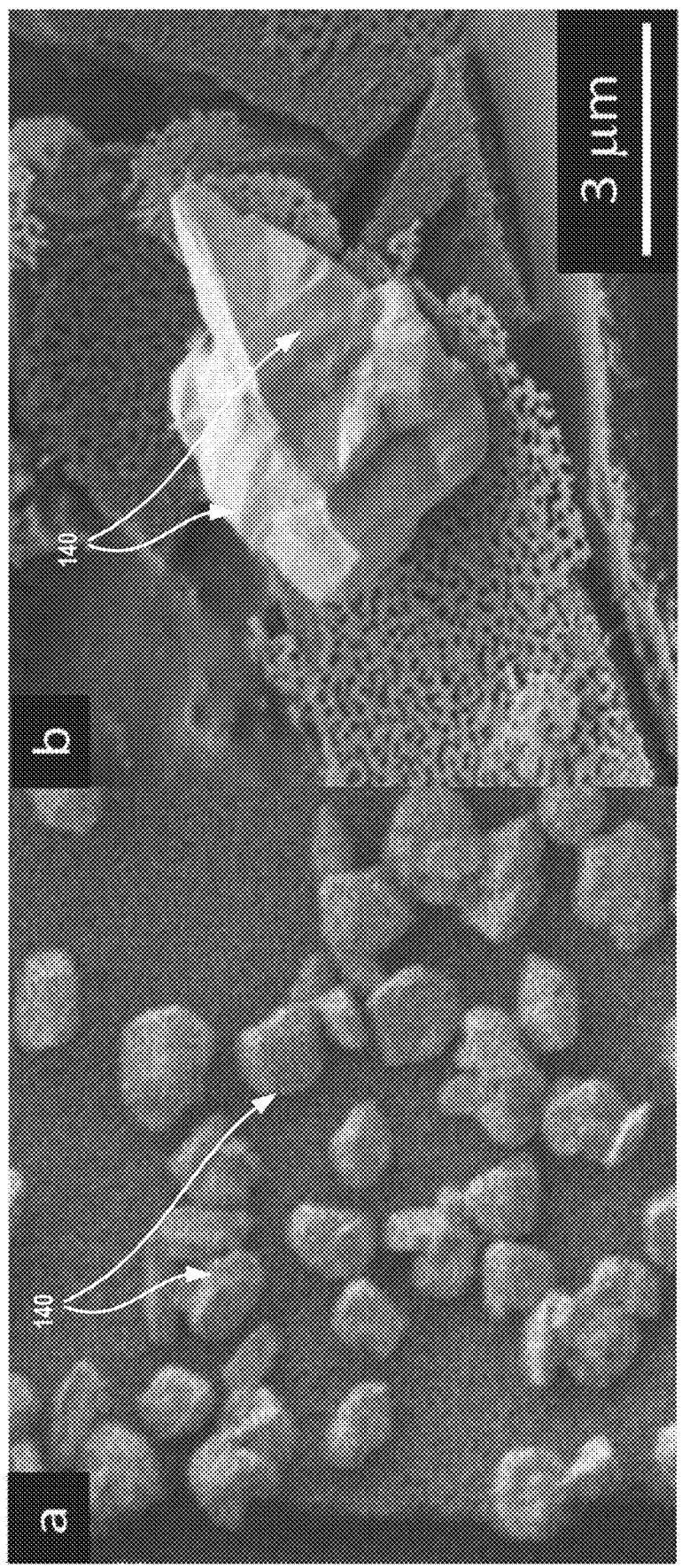
FIG. 12a is a SEM image, identical scale to FIG. 12b, depicting the relative size of loaded CuO synthesized through one loading and heat treatment cycle in accordance with an embodiment of the present invention.
FIG. 12b is a SEM image depicting the relative size of loaded CuO synthesized through two loading and heat treatment cycles separated by an acid wash in accordance with an embodiment of the present invention.

With reference to FIG. 12a a SEM image, identical scale to FIG. 12b, depicting the relative size of loaded CuO synthesized through one loading and heat treatment cycle in accordance with an embodiment of the present invention is shown. A SEM image showing a representative size distribution of loaded CuO crystals 140 after one loading and heat treatment cycle with no acid washes. The average length of the longest dimension of the CuO crystals 140 was determined to be 1.2±0.3 µm based on analysis of 15 crystals found in two separate microspheres.

With reference to FIG. 12b is a SEM image depicting the relative size of loaded CuO synthesized through two loading and heat treatment cycles separated by an acid wash in accordance with an embodiment of the present invention is shown. A SEM image showing a representative CuO structure found loaded within a microsphere 10 undergoing two loading and heat treatment cycles separated by a 0.5M HCl soak. The average length of the longest dimension of these crystals was determined to be 3.9±1.1 µm based on analysis of 15 CuO structures 140 found in five separate microspheres.

Direct loading of functional materials is still possible if the dimensions of the material are small compared to the diameter of the microsphere wall porosity. Candidate materials consist of molecules or sub-nanometer particles which often remain dispersed in a solvent to exhibit functionality. Thus, the loading solution itself can be considered a functional cargo which substantially broadens the realm of material candidates for security features. The loading process is greatly simplified for this form of composite as there is no need for in situ synthesis.

Figure 13:
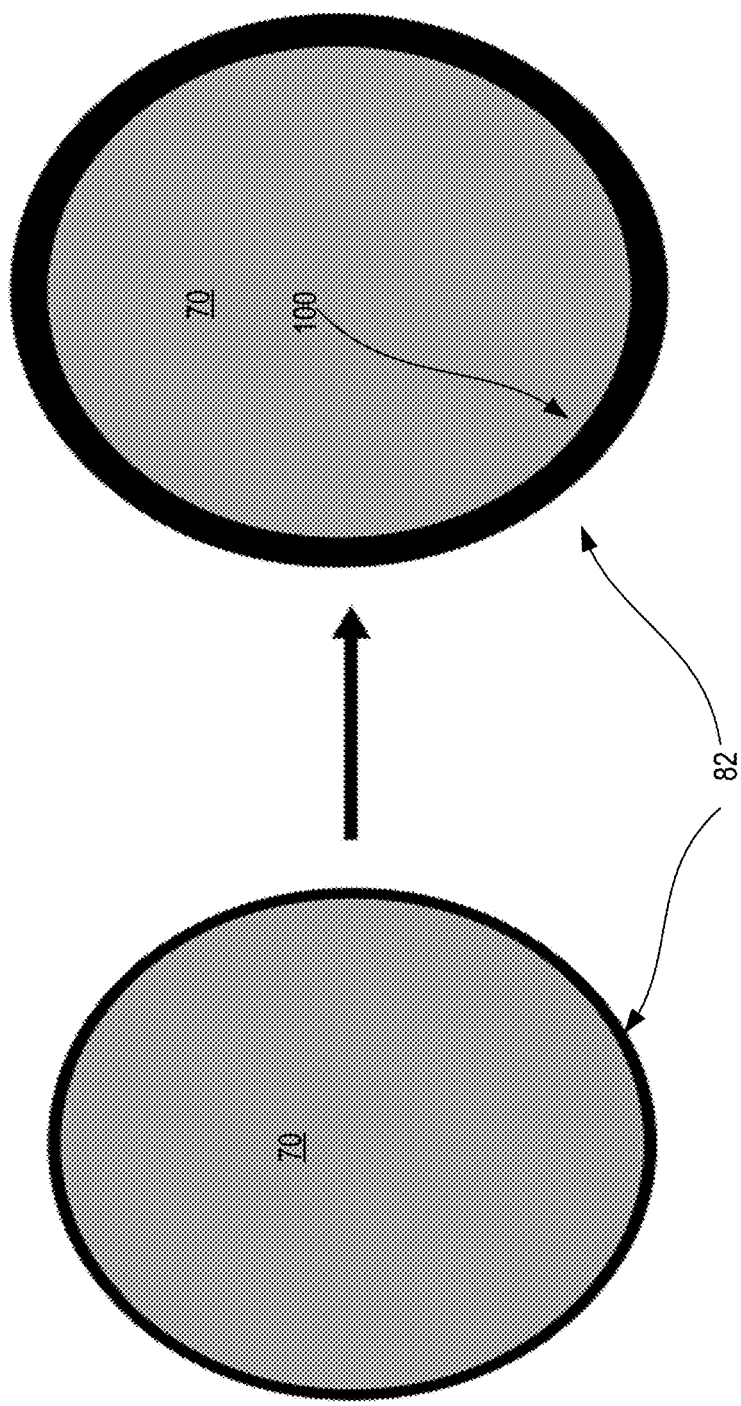
FIG. 13 is a pictorial illustration of loaded functional solutions being retained within microspheres by coatings in accordance with an embodiment of the present invention.

With reference to FIG. 13 a pictorial illustration of loaded functional solutions being retained within microspheres by coatings in accordance with an embodiment of the present invention is shown. The need for a means of entrapping the solution 70 within microspheres 10 complicates the situation while also providing the option to impart additional functionalities. Like the solid cargo composites considered above, solution-loaded microspheres 82 could respond to tampering by releasing the payload for detection. The use of functional coatings 100 could also allow for the controlled out-diffusion of the payload after a certain period or when exposed to a certain environment (e.g., oxygenated atmosphere or acidic/basic pH). Such functionality would be particularly useful for the development of covert taggants in liquid products, such as paints and inks.

As initial steps in developing this complex material system, microspheres 10 were loaded with a fluorescent solution consisting of a fluorescent molecular probe, 8-anilinonaphthalene-1-sulfonic acid (ANS), bound to a commercially available and inexpensive coderived protein, bovine serum albumin (BSA). Intense blue emission occurs only when ANS is bound to folded BSA and excited by ultraviolet (UV) light. The fluorescent BSA/ANS solution was made by adding two drops of 0.1M aqueous ANS solution to 100 mL of 15 µM aqueous BSA solution. Wet vacuum loading was conducted at room temperature. The magnitude of the reduced pressure was 75 kPa below ambient pressure. The soak periods lasted for 60 min. Three evacuation/vent cycles were performed before the microspheres 10 were filtered from the fluorescent solution using vacuum filtration. Three samples were prepared for characterization. The first was unrinsed during the filtration step while the second and third samples were rinsed with 10 mL and 50 mL of distilled water, respectively. This step was taken to analyze the retention of fluorescent solution on the interior of the microspheres 10 when coatings, or other means of pore blockage, are absent. The BSA/ANS-loaded microspheres were analyzed by a Visual Spectral Comparator (VSC). VSC obtained the fluorescent emission spectra and the visual appearance of the three microspheres samples when excited by 365 nm UV light.

Figures 15A, 15B:
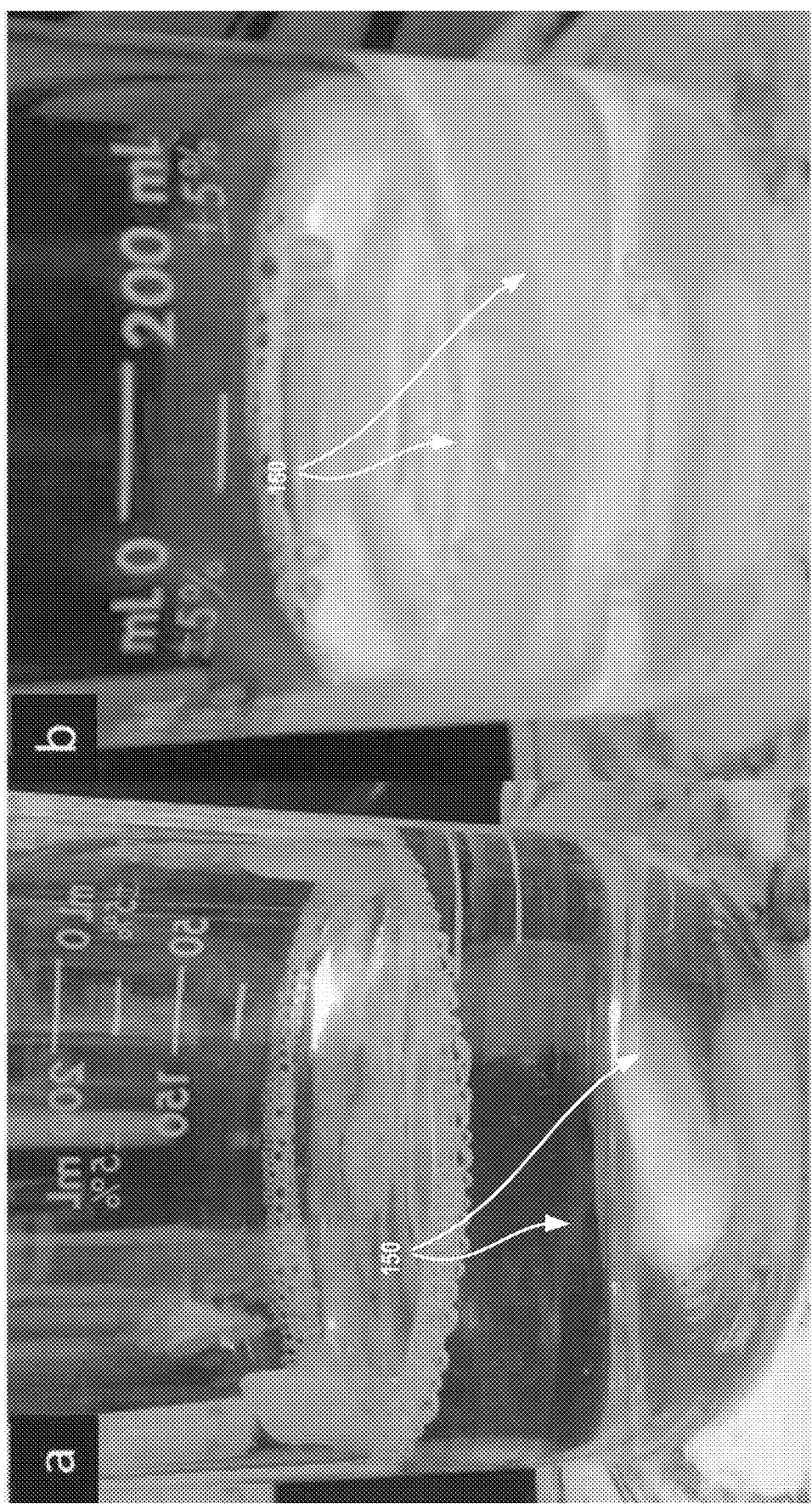
FIG. 15a is a pictorial illustration of a BSA/ANS solution when illuminated by white light in accordance with an embodiment of the present invention.
FIG. 15b is a pictorial illustration of a BSA/ANS solution when illuminated by UV light in accordance with an embodiment of the present invention.

With reference to FIG. 15a a pictorial illustration of a BSA/ANS solution when illuminated by white light in accordance with an embodiment of the present invention is shown. FIG. 15 shows the fluorescent BSA/ANS solution used to load microspheres 10. In FIG. 15a, the solution 150 is illuminated under white light. The solution is transparent, and no fluorescent emission is observed.

With reference to FIG. 15b a pictorial illustration of a BSA/ANS solution when illuminated by a UV lamp in accordance with an embodiment of the present invention is shown. In FIG. 15b, the solution 150 is illuminated by a UV lamp. Clearly, the solution takes on a bright blue color due to fluorescent emission from the BSA/ANS particles. This intense, optical response from a dilute, aqueous solution demonstrates the functionality desired from BSA/ANS-loaded microspheres. The emission spectra of the BSA/ANS-loaded microspheres was obtained to characterize the material's fluorescence and to establish if water rinsing resulted in removal of payload solution from the microspheres.

Figure 16:
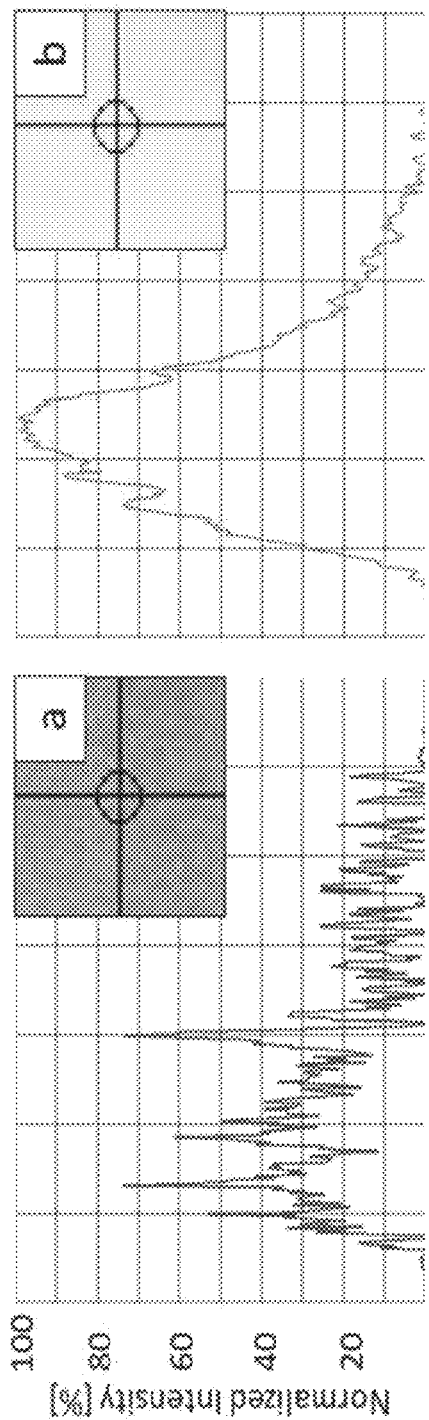
FIG. 16a is a pictorial illustration of emission spectra and visual appearance of unloaded microspheres in accordance with an embodiment of the present invention.
FIG. 16b is a pictorial illustration of emission spectra and visual appearance of loaded microspheres unwashed in accordance with an embodiment of the present invention.
FIG. 16c is a pictorial illustration of emission spectra and visual appearance of loaded microspheres with 10 mL distilled water wash in accordance with an embodiment of the present invention.
FIG. 16d is a pictorial illustration of emission spectra and visual appearance of loaded microspheres with 50 mL distilled water wash in accordance with an embodiment of the present invention.
Figure 16:
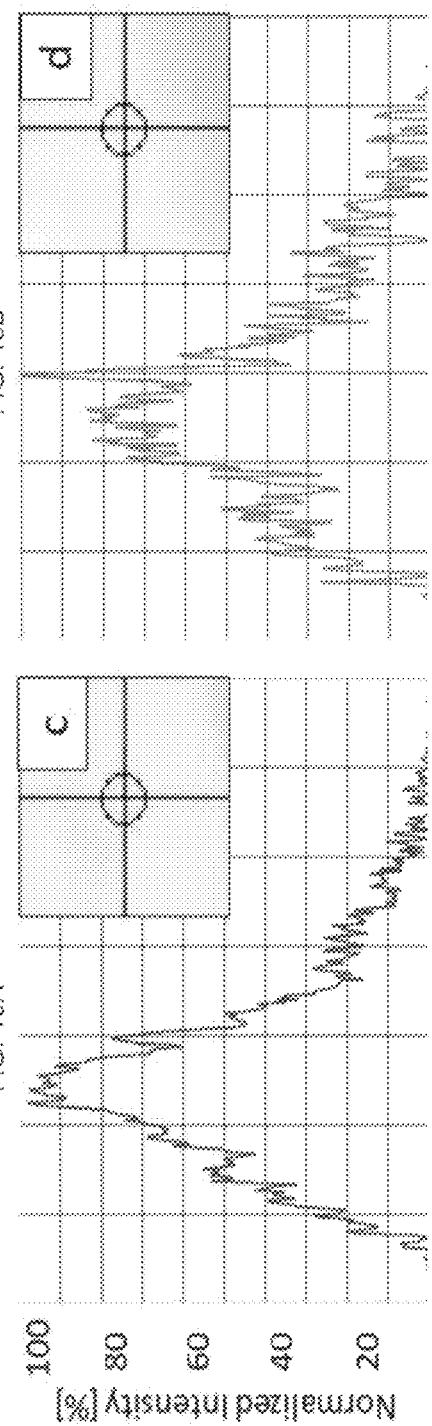

FIG. 16 provides the emission spectra and visual appearance of four samples: (a) unloaded and dry microspheres; (b) unwashed, BSA/ANS-loaded microspheres; (c) BSA/ANS-loaded microspheres, washed with 10 mL of distilled water; and (d) BSA/ANS-loaded microspheres, washed with 50 mL of distilled water.

All BSA/ANS-loaded microspheres exhibit a distinct blue/green emission peak at roughly 525 nm. The control sample (unloaded, dry microspheres) does not exhibit a clear emission peak although there is a broad and relatively weak emission centered around 500 nm. Based on these results, the presence of BSA/ANS on or within the loaded microspheres is confirmed. Washing clearly influences the optical response of the loaded microspheres as a broadening of the emission peaks and change in visual appearance occurs. Potentially this is due to an increase in BSA/ANS concentration owing to a loss of water on the interior of the microspheres. There are also potential interactions between BSA, which is known to adsorb to silica, with the microspheres which could influence fluorescence. Further work is needed to identify the cause of fluorescent shifts. Most critically, coatings need to be developed to effectively contain the solution on the interior of the microspheres prior to application.

Figure 14:
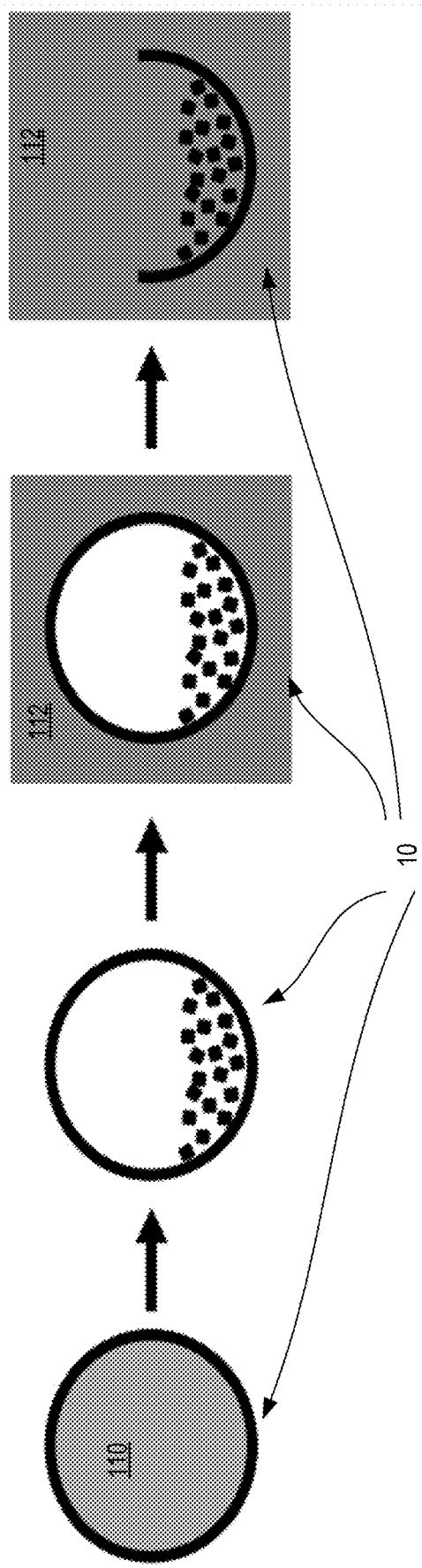
FIG. 14 is a pictorial illustration of loaded reactive materials exhibiting functional responses when exposed to an initiator, such as a matrix material in accordance with an embodiment of the present invention.

With reference to FIG. 14 a pictorial illustration of loaded reactive materials exhibiting functional responses when exposed to an initiator, such as a matrix material in accordance with an embodiment of the present invention is shown. As was addressed in the previous sections, the primary benefit to creating composite material systems out of microspheres 10 is the ability of the microspheres 10 to act as protective capsules which can isolate loaded materials from the surrounding environment until released. This property of microspheres 10 allows for the loading of reactive materials, which alone do not exhibit unique properties, but when exposed to an initiator material develop functional responses to stimuli, such as fluorescence under UV excitation. Microspheres 10 loaded with reactive cargo represent the most advanced form of tamper-responsive composite materials and offer the potential for security functionality. In these systems, not only must the payload be released from the microsphere 10 through mechanical abrasion or out-diffusion, but the cargo must then react with an initiator before stimulated functional responses can be detected. An initiator may be present in a test solution deployed during product authentication, within the security feature as a part of a matrix material, or even within a second population of loaded microspheres.

To investigate the ability to load and then release a reactive material from within the microspheres into an environment containing an initiator, microspheres 10 were loaded with ANS and then dispersed in a BSA solution. Unlike the functional solution system considered previously, fluorescence will not occur until the exterior BSA and interior ANS contact each other. Microspheres 10 were loaded with 0.1M aqueous ANS solution 110 through wet vacuum loading. The reduced pressure environment was held at 75 kPa below ambient pressure. The soak duration was 30 min. Two evacuation/vent cycles were performed before the microspheres 10 were vacuum filtered from the ANS solution 110. The ANS-loaded microspheres were added to 4 mL of 15 µM aqueous BSA solution 112 while being illuminated by UV light. Then, the microspheres 10 were filtered from the BSA solution 112, rinsed with 10 mL of distilled water, and dispersed in 4 mL of fresh 15 µM BSA solution. Again, the solution was observed under UV excitation. After 5 min, the ANS-loaded microspheres were placed in an ultrasonic bath while dispersed in BSA solution for 60 s. Then the vial containing the microspheres and BSA solution was vigorously shaken and placed under UV illumination for observation. After 5 min, the microspheres were filtered from the BSA solution and dried. The response of the ANS-loaded microspheres to UV excitation while dispersed in BSA solution was analyzed visually and documented by photographs. Observation of fluorescence at any stage of the process would signify contact between the loaded reactive material and the surrounding initiator material. The dried microspheres were characterized by SEM to evaluate the effectiveness of sonication as means of breaking the microspheres to release the reactive payload.

Figures 17A, 17B, 17C:
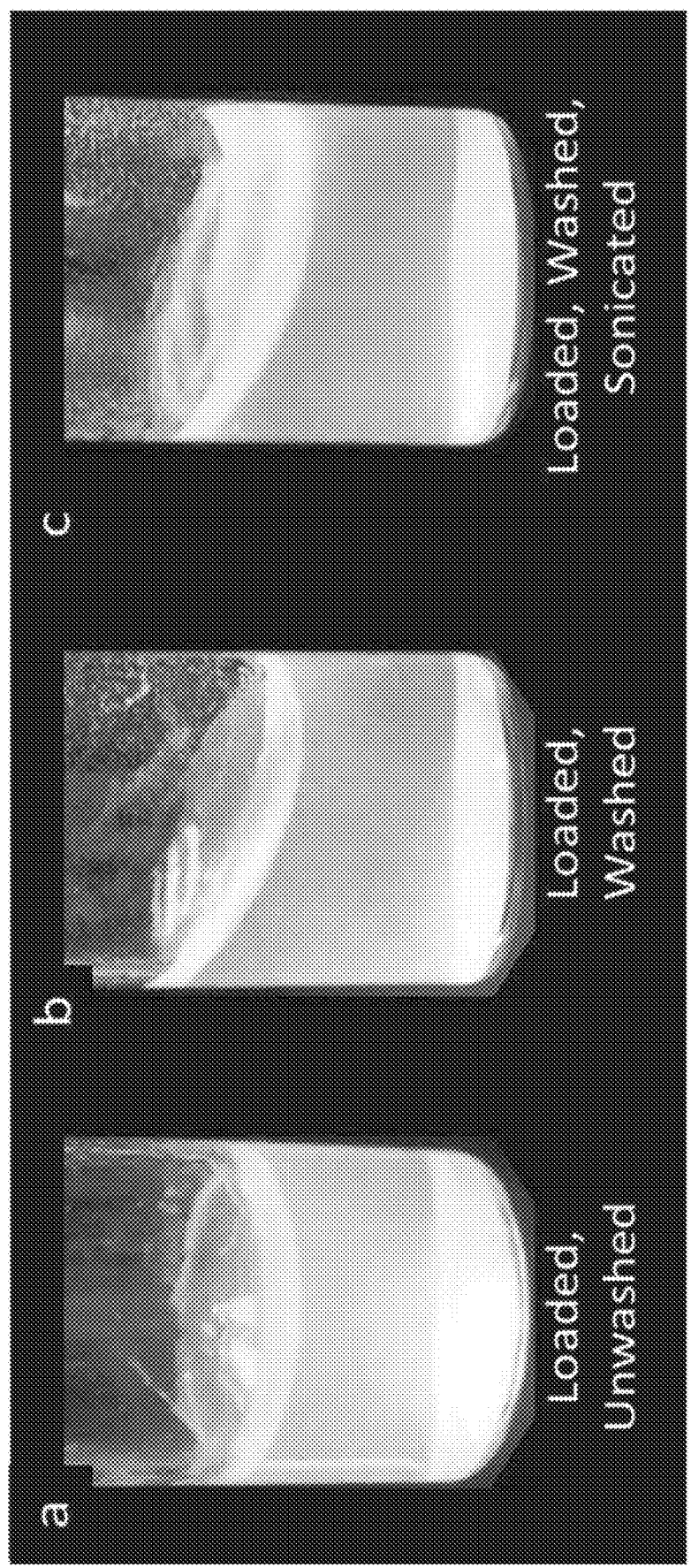
FIG. 17a-c is a pictorial illustration of a comparison of optical response of ANS-loaded microspheres dispersed in BSA solution in accordance with an embodiment of the present invention.

With reference to FIG. 17a-c a pictorial illustration of a comparison of optical response of ANS-loaded microspheres dispersed in BSA solution in accordance with an embodiment of the present invention is shown. FIG. 17 depicts the appearance of the ANS-loaded microspheres while dispersed in BSA solution under UV illumination. The microspheres in FIG. 17a have been loaded, filtered, and then transferred immediately to the BSA solution. Blue fluorescent emission was observed immediately after the microspheres contacted the solution. FIG. 17b shows the optical response of the dispersion when the ANS-loaded microspheres were washed prior to exposure to the BSA solution. A lack of blue fluorescence was observed directly although the image in FIG. 17b does not present this effectively due to scattering of the incident UV light. In FIG. 17c, the optical response of the loaded and washed microspheres is shown 5 min after sonication. Blue fluorescence was again observed but only after the microspheres soaked in solution for 5 min. Changes in fluorescence were clear during direct visual observation of the samples. However, in FIG. 17, only subtle changes in color between the situations in which fluorescence was observed to have occurred (17a and 17c) and the situation in which fluorescence did not occur (17b) can be observed.

The immediate fluorescent response in FIG. 17a was expected since ANS, present on the exterior of microspheres due to an absence of washing, was free to interact and bind with BSA in solution. The lack of fluorescent response in FIG. 17b suggests any exterior ANS was washed away and any ANS present on the interior of the microspheres was kept isolated from the BSA solution by the microsphere walls. The delay in fluorescent response observed for the sample in FIG. 17c was unexpected. The use of sonication and shaking was expected to fracture the microspheres 10 and expose the loaded, reactive ANS to the BSA initiator. The delay in optical response suggested the payload was not immediately exposed to the surrounding solution and, instead, diffusion may be occurring through the porosity of intact microspheres 10. SEM was used to analyze the state of the microspheres exhibiting a delayed fluorescent response.

Figure 18:
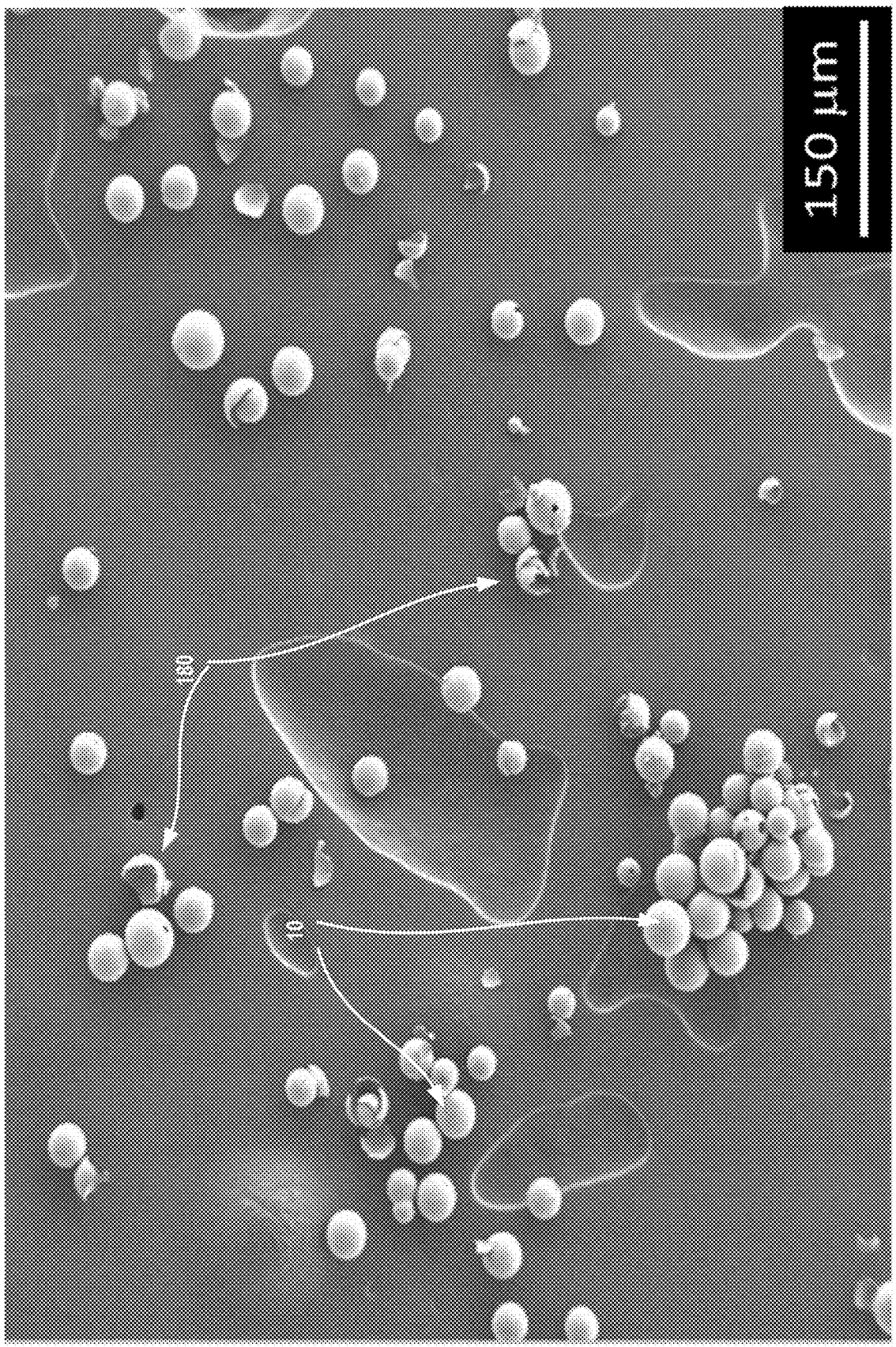
FIG. 18 is a SEM image of ANS-loaded, washed, and sonicated microspheres in accordance with an embodiment of the present invention.

FIG. 18 shows a representative SEM image of the microsphere sample on adhesive carbon tape. Some microsphere shards 180 can be observed but the number of microspheres 10 appearing intact is substantial. This supports the theory the time delay in fluorescent response may have been caused by insignificant microsphere fracture followed by ANS or BSA transport through the wall porosity. This points to the need for a more effective technique to evaluate reactive material release but also encourages the application of microspheres to security printing as it demonstrates the robustness of the microspheres 10 when dispersed in solution and subjected to ultrasonic frequencies.

Coating of microspheres 10 can be performed to impart additional desirable characteristics including improved mechanical durability and functional properties (e.g., chemical, thermal, optical, electrical and/or magnetic). A process to coat porous wall hollow microspheres 10 with a metallic nickel-phosphorous (Ni—P) alloy can be demonstrated. This coating has the potential to improve mechanical strength, serve as a barrier to optical excitation of microsphere payloads, to impart magnetic functionality to microspheres.

An electroless Ni-plating process can be used. In this process, 0.050 g of microspheres 10 were immersed in a tin bath consisting of 50 mL of 0.1M HCl and 1.128 g $SnCl_2.2H_2O$ (0.1M). After soaking for five minutes, the microspheres 10 were filtered while rinsing with distilled water. The microspheres 10 were then transferred into a palladium bath consisting of 50 mL of 0.25M HCl and 0.0124 g $PdCl_2$ (0.0014M). After a five-minute soak period, the microspheres 10 were filtered and rinsed with distilled water. Then, the microspheres 10 were transferred into a nickel-plating bath consisting of 50 mL of distilled water, 1.498 g $NiSO_4.6H_2O$ (0.114M), 1.272 g $NaH_2PO_2.H_2O$ (0.240M), 0.794 g $Na_3C_6H_5O_7.2H_2O$ (0.054M), and 0.1 mg thiourea. The nickel-plating bath was heated to 70-80° C. and kept at a pH of 7-8 using $NH_4OH$ as a buffer. These bath conditions were maintained for one hour, then the solution was filtered, rinsed, and dried overnight. Finally, the coated microspheres were sonicated in water for 10 minutes to remove excess surface debris.

Figure 19:
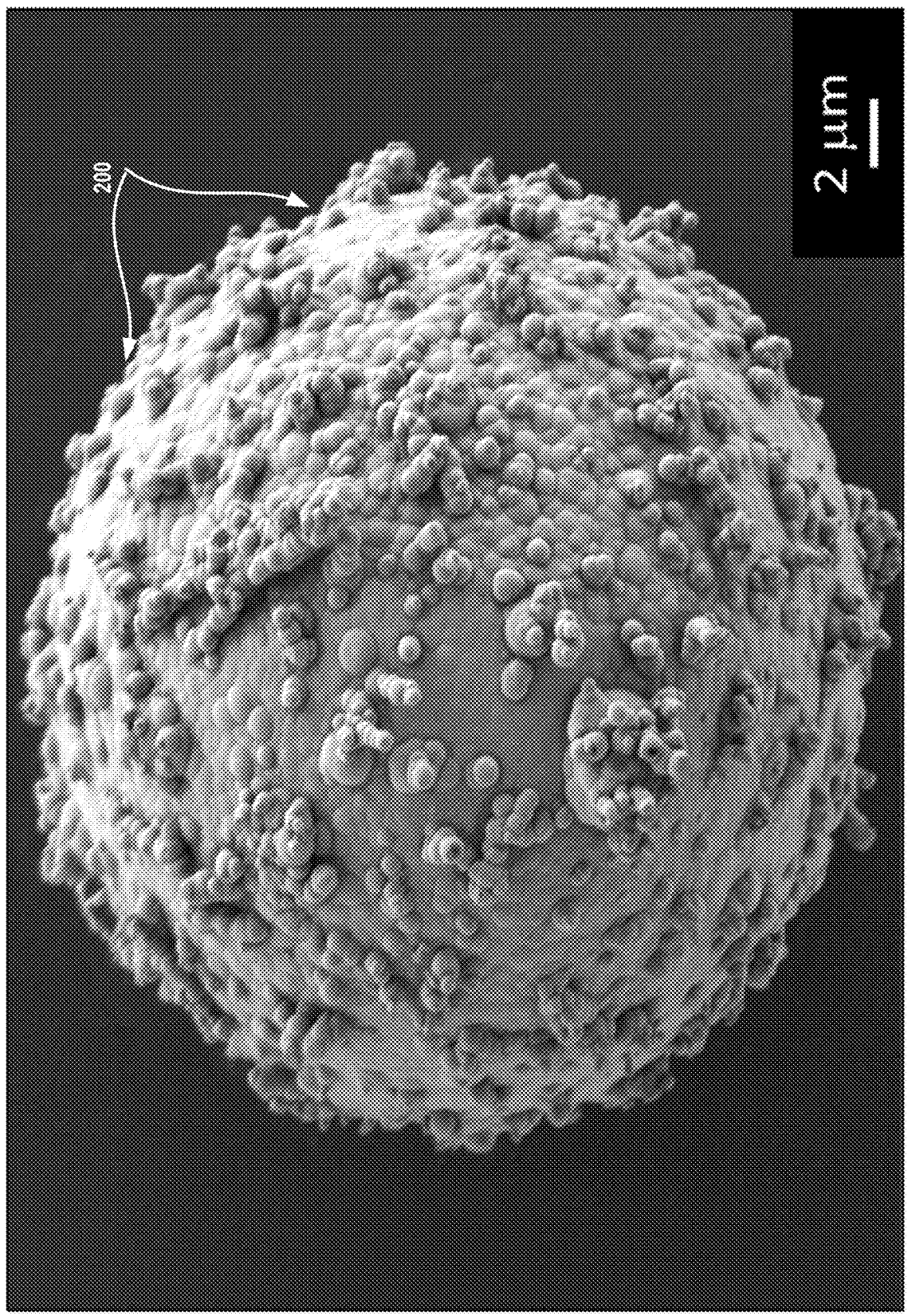
FIG. 19 is a SEM image showing the presence of a rough metallic coating on a microsphere in embodiments of the present invention.

With reference to FIG. 19 a SEM image showing the presence of a rough metallic coating on a microsphere in embodiments of the present invention is shown. The Ni—P coatings 200 on the microspheres 10 were characterized using SEM, EDS, XRD, and VSC. EDS analysis confirmed the coating was a Ni—P alloy containing 4.6 wt % phosphorous. XRD confirmed the coating consisted of a face-centered cubic crystal structure with lattice spacing matching Ni.

Figure 20:
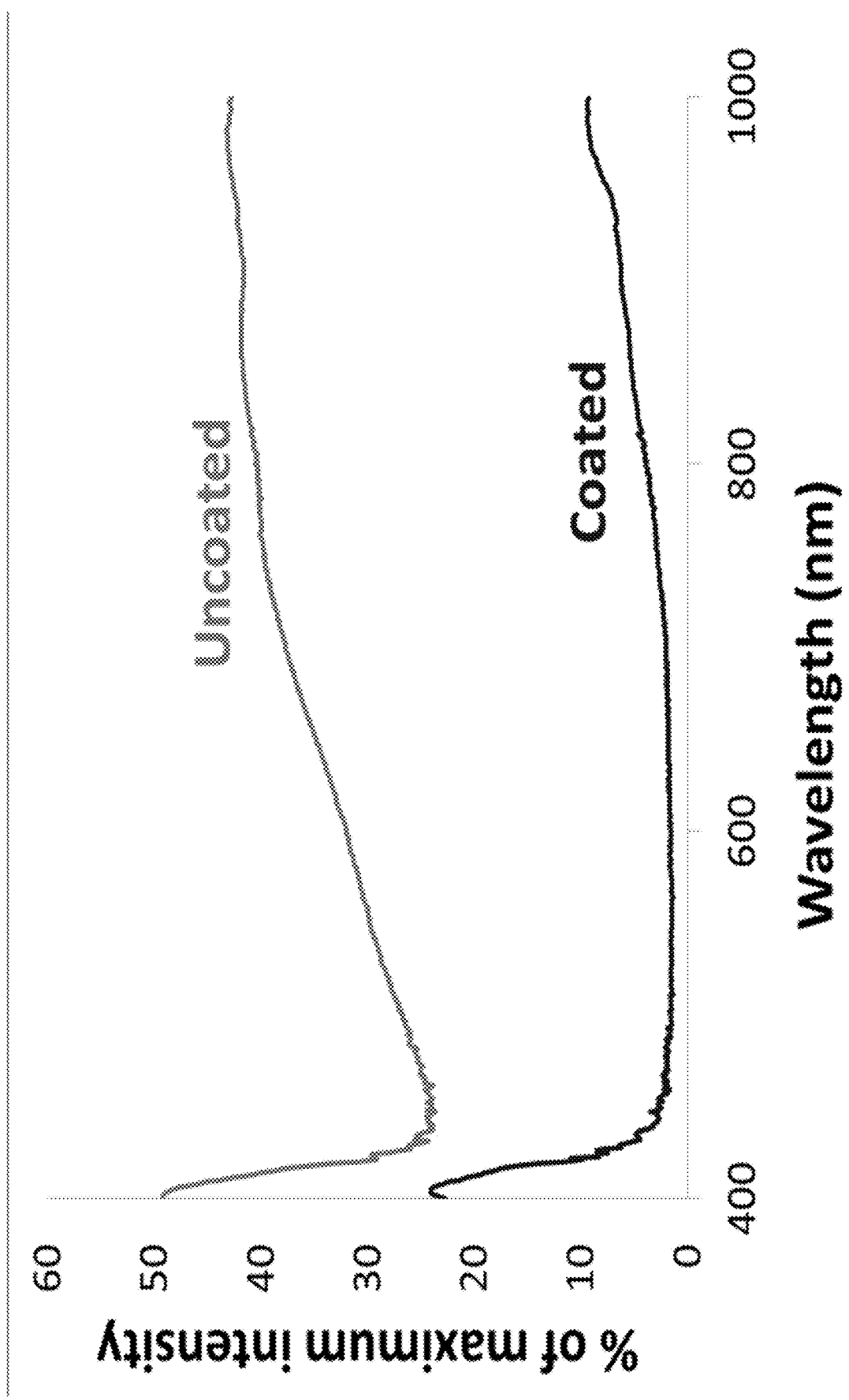
FIG. 20 is a plot of transmitted light intensity as a function of light wavelength in embodiments of the present invention.

With reference to FIG. 20 a plot of transmitted light intensity as a function of light wavelength in embodiments of the present invention are shown. VSC was used to measure the transmittance of visible light through uncoated and coated microspheres 10. The decrease in transmitted light intensity for the Ni—P microspheres demonstrates the ability to form opaque coatings which may be used to mask functional payloads within microsphere interiors.

Figures 21A, 21B:
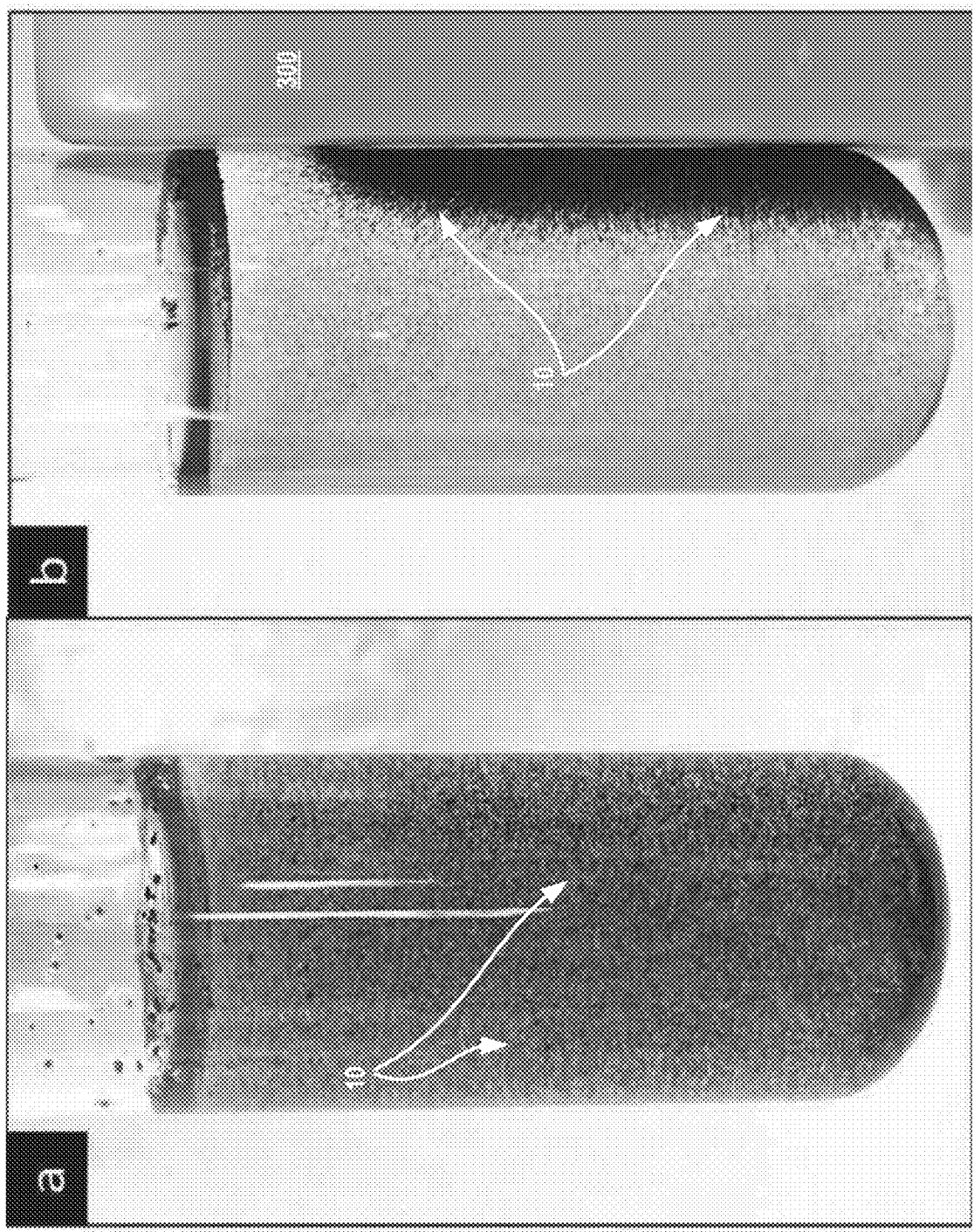
FIG. 21a is a test tube containing coated microspheres dispersed in water as depicted in the absence of an external magnet in embodiments of the present invention.
FIG. 21b is a test tube containing coated microspheres dispersed in water as depicted in the presence of an external magnet in embodiments of the present invention.

With reference to FIG. 21 a test tube containing coated microspheres dispersed in water is depicted in the absence and presence of an external magnet in embodiments of the present invention is shown. Additionally, the application of the Ni—P coatings introduced magnetic properties to the microspheres. The coated microspheres 10 are observed to be attracted to the magnet 300.

The evidence presented here demonstrates the ability to create multiple forms of microsphere composites for use in next generation security features activated by tampering. The deployment configurations and processing routes studied were chosen to highlight microsphere characteristics introducing new and robust security functionalities to features and product authentication methods. Specifically, the ability to load microspheres with precursor functional materials, functional materials and reactive functional materials was demonstrated. Key conclusions drawn from these studies include:

(i) Solution-based loading of microspheres results in a yield of loaded microspheres suitable for most microscopic characterization techniques.

(ii) The CuO synthesis and BSA/ANS fluorescent emission results show loaded solutions can be retained within microspheres for limited yet significant amounts of time. This suggests both more complex in situ syntheses of functional solid materials and the coating of solution-loaded microspheres are possible.

(iii) Preliminary results from the loading of microspheres with reactive functional materials teach a system having complex, hierarchical security features.

Evidence illustrates the versatility of microspheres and motivate their application to anti-counterfeiting technologies. If the threats posed by counterfeit products are to be mitigated, the development of advanced functional materials, such as loaded microspheres, is beneficial.

The invention is not to be limited to the embodiments described herein. The foregoing description has been presented for purposes of illustration and description. It is not intended to be an exhaustive list or limit any of the invention to the precise forms disclosed. It is contemplated other alternatives or exemplary aspects are considered included in the invention. The description is merely examples of embodiments, processes or methods of the invention. It is understood any other modifications, substitutions, and/or additions can be made, which are within the intended spirit and scope of the invention.

What is claimed is:

1. An event detection composite comprising:
a first plurality of glass microspheres, each microsphere of the first plurality of glass microspheres comprising a first porous outer wall surrounding a first hollow central core comprising a first microsphere volume;
a functional material;
a payload within each microsphere volume, the payload having the functional material encapsulated within each hollow central core and a payload volume relative to the microsphere volume as a result of a microsphere loading factor;
wherein the functional material is disposed within each hollow central core as a result of a payload loading cycle method comprising mechanical, thermal or chemical method steps of drawing the payload through each porous outer wall and into each microsphere volume, the payload loading cycle method capable of maximizing the microsphere loading factor;
a host material wherein the first plurality of glass microspheres is dispersed in the host material;
the event detection composite exhibiting one or more properties responsive to specific stimuli, the event detection composite configured to change the one or more properties in response to the specific stimuli selected from a group comprising a mechanical stimulus, an optical stimulus, an electrical stimulus, a magnetic stimulus, a thermal stimulus, and a chemical stimulus;
wherein a change in the one or more properties elicits a response based at least in part on the microsphere loading factor;
a reactive material;
a second plurality of glass microspheres comprising a second porous outer wall surrounding a second hollow central core comprising a second microsphere volume, each glass microsphere of the second plurality of glass microspheres housing the reactive material and dispersed in the host material wherein the reactive material and the functional material are configured to react to elicit the response.

2. The event detection composite of claim 1, further comprising:
a coating on each first porous outer wall of the first plurality of glass microspheres, wherein the coating exhibits one or more functional properties responsive to the specific stimuli.

3. The event detection composite of claim 1, further comprising:
a coating on each first porous outer wall of the first plurality of glass microspheres for retaining the functional material within each first microsphere volume.

4. An event detection system comprising:
a first plurality of glass microspheres, , wherein each glass microsphere of the first plurality of glass microspheres comprises a spherical porous outer wall and a hollow central core comprising a microsphere volume bounded by the spherical porous outer wall;
a functional material;
a host material;
a payload within each microsphere volume, the payload having the functional material and having a payload volume relative to each microsphere volume as a result of a microsphere loading factor; and
wherein the functional material is disposed within at least each hollow central core of each glass microsphere of the first plurality of glass microspheres as a result of a payload loading cycle method comprising one or more mechanical, thermal, or chemical variables for drawing the payload through each spherical porous outer wall and into each microsphere volume and capable of maximizing the microsphere loading factor, the variables comprising a pressure value, a temperature value, a soak time, a number of evacuation cycles, a number of venting cycles, a number of stirring cycles, a number of washing cycles, a number of drying cycles, a size and a morphology of pores within each spherical porous outer wall;
a reactive material;
a second plurality of glass microspheres, each glass microsphere of the second plurality of glass microspheres housing the reactive material;
a composite comprising the host material, the first plurality of glass microspheres housing the functional material, and the second plurality of glass microspheres housing the reactive material; wherein the reactive material and the functional material are configured to combine as a result of specific stimuli and to elicit a response to the specific stimuli based at least in part on the microsphere loading factor.

5. The event detection system of claim 4, wherein the functional material exhibits one or more functional properties selected from a group consisting of an optical property, an electrical property, a magnetic property, a thermal property, and a chemical property.

6. The event detection system of claim 4, further comprising:

a coating on each spherical porous outer wall of each glass microsphere of the first plurality of glass microspheres, wherein the coating comprises one or more functional properties responsive to the specific stimuli selected from a group of stimuli comprising a mechanical stimulus, an optical stimulus, an electrical stimulus, a magnetic stimulus, a thermal stimulus, and a chemical stimulus.

7. The event detection system of claim 4, further comprising:

a coating on each spherical porous outer wall of each microsphere of the first plurality of glass microspheres for retaining the functional material within each microsphere volume.

* * * * *